United States Patent
Buell et al.

(10) Patent No.: US 10,898,391 B2
(45) Date of Patent: Jan. 26, 2021

(54) COMPACT TAMPON APPLICATOR WITH TWO-PIECE PLUNGER

(71) Applicant: Edgewell Personal Care Brands, LLC, Chesterfield, MO (US)

(72) Inventors: Sezen Buell, Waldwick, NJ (US); Joseph Fedora, Meriden, CT (US); James McCandless, Durham, CT (US); Hassan Mohamed, Ridgewood, NJ (US); Peter Preisner, Quinton, VA (US)

(73) Assignee: EDGEWELL PERSONAL CARE BRANDS, LLC, Chesterfield, MO (US)

( * ) Notice: Subject to any disclaimer, the term of this patent is extended or adjusted under 35 U.S.C. 154(b) by 752 days.

(21) Appl. No.: 15/560,670

(22) PCT Filed: Nov. 10, 2015

(86) PCT No.: PCT/US2015/059889
§ 371 (c)(1),
(2) Date: Sep. 22, 2017

(87) PCT Pub. No.: WO2016/077307
PCT Pub. Date: May 19, 2016

(65) Prior Publication Data
US 2018/0104113 A1      Apr. 19, 2018

Related U.S. Application Data

(60) Provisional application No. 62/077,397, filed on Nov. 10, 2014.

(51) Int. Cl.
*A61F 13/26* (2006.01)
*A61F 13/551* (2006.01)

(52) U.S. Cl.
CPC .......... *A61F 13/263* (2013.01); *A61F 13/266* (2013.01); *A61F 13/551* (2013.01); *A61F 13/5511* (2013.01)

(58) Field of Classification Search
CPC .. A61F 13/266; A61F 13/551; A61F 13/5511; A61F 13/84; A61F 13/263
See application file for complete search history.

(56) References Cited

U.S. PATENT DOCUMENTS

| | | | |
|---|---|---|---|
| 4,048,998 A * | 9/1977 | Nigro | A61F 13/263 604/14 |
| 4,411,647 A * | 10/1983 | Sakurai | A61F 13/263 604/16 |
| 4,921,474 A * | 5/1990 | Suzuki | A61F 13/263 604/16 |
| 7,704,242 B2 * | 4/2010 | Lemay | A61F 13/26 604/11 |

(Continued)

FOREIGN PATENT DOCUMENTS

| CN | 88102829 A | 11/1988 |
|---|---|---|
| CN | 2154035 | 1/1994 |

(Continued)

OTHER PUBLICATIONS

Korean Office Action for Application No. 10-2017-7015935, dated Oct. 25, 2018.

(Continued)

*Primary Examiner* — Susan S Su

(57) ABSTRACT

A compact applicator has a two-piece telescoping plunger. The compact applicator, with such telescoping plunger, has a full-size barrel region while maintaining an overall applicator length that is the same and/or slightly shorter than current known compact applicators. In a non-deployed configuration, the inner sleeve of the plunger is generally telescoped within the outer sleeve of the plunger, and the outer sleeve of the plunger is generally telescoped within the applicator barrel.

15 Claims, 14 Drawing Sheets

(56) References Cited

U.S. PATENT DOCUMENTS

| | | | | |
|---|---|---|---|---|
| 8,308,675 | B2* | 11/2012 | Cettina | A61F 13/266 604/15 |
| 2006/0217652 | A1* | 9/2006 | Heuer | A61F 13/26 604/15 |
| 2007/0167902 | A1* | 7/2007 | Edgett | A61F 13/266 604/15 |
| 2011/0273727 | A1* | 11/2011 | Seki | A61F 13/2051 356/634 |
| 2012/0029415 | A1* | 2/2012 | Wada | A61F 13/263 604/15 |
| 2012/0059306 | A1* | 3/2012 | Tamburin | A61F 13/263 604/14 |
| 2014/0155810 | A1* | 6/2014 | Buell | A61F 13/34 604/16 |
| 2014/0180193 | A1* | 6/2014 | Dougherty | A61F 13/26 604/16 |
| 2015/0223993 | A1* | 8/2015 | Ito | A61F 13/266 604/15 |

FOREIGN PATENT DOCUMENTS

| | | |
|---|---|---|
| CN | 101346114 A | 1/2009 |
| EP | 0223072 A1 | 5/1987 |
| EP | 0349222 A2 | 1/1990 |
| GB | 2081586 A1 | 2/1982 |
| GB | 2120945 A1 | 12/1983 |
| WO | 2010086804 A2 | 8/2010 |

OTHER PUBLICATIONS

Unofficial English translation of Mexican Office Action issued in connection with the corresponding MX Application No. MX/a/2017/005985 dated Jan. 27, 2020.

PCT International Preliminary Report on Patentability issued in connection with PCT/US2015/059889 dated May 16, 2017.

PCT Search Report and Written Opinion issued in connection with PCT/US2015/059889 dated Feb. 17, 2016.

European Office Action issued in connection with the corresponding EP Application No. 15797559.0 dated Oct. 23, 2018.

European Office Action issued in connection with the corresponding EP Application No. 15797559.0 dated Sep. 20, 2019.

Unofficial English translation of Chinese Office Action issued in connection with the corresponding CN Application No. 201580061223.1 dated Dec. 31, 2019.

Unofficial English translation of Chinese Search Report issued in connection with the corresponding CN Application No. 201580061223.1 dated Dec. 31, 2019.

* cited by examiner

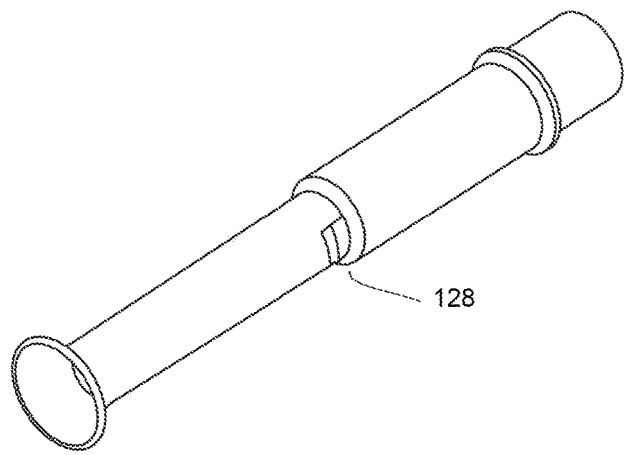
FIG. 25
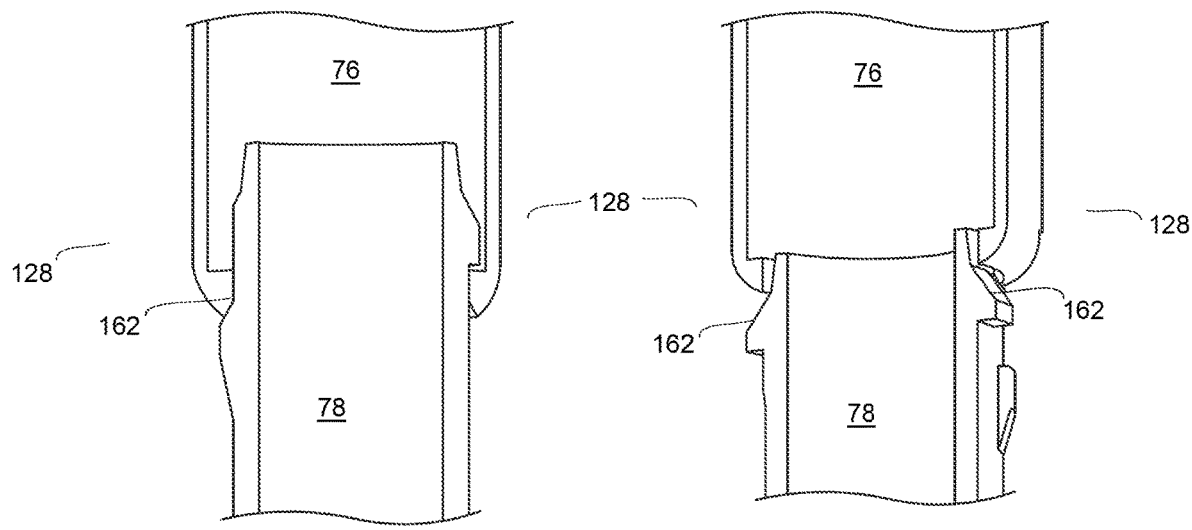
FIG. 26
FIG. 27

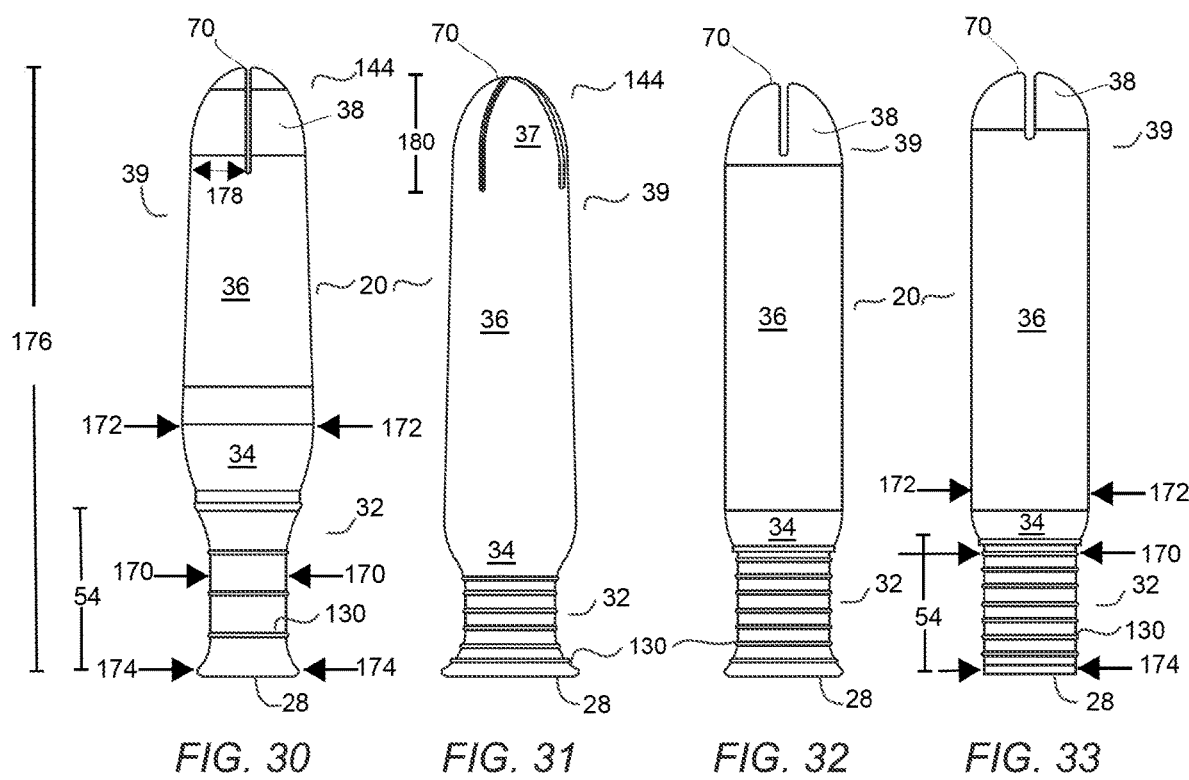

COMPACT TAMPON APPLICATOR WITH TWO-PIECE PLUNGER

CROSS-REFERENCE TO RELATED APPLICATIONS

This application claims the benefit of priority to U.S. Provisional Patent Application Ser. No. 62/077,397 filed on Nov. 10, 2014, the contents of which are incorporated by reference herein.

BACKGROUND OF THE INVENTION

1. Technical Field

The present disclosure relates to tampon applicators having a plunger in general, and to tampon applicators that include a two piece telescoping plunger in particular.

2. Background Information

Some tampons are available in a format that includes an applicator to facilitate insertion of the tampon. There are a variety of different types of tampon applicators available. For example, some types of applicators include a barrel portion and a plunger. Prior to use, the tampon is disposed within an interior cavity of the barrel. The plunger is operable to move relative to the barrel to expel the tampon during insertion. Some applicators, such as that disclosed in U.S. Pat. No. 4,921,474, utilize a two-piece telescoping plunger. Applicators having a plunger that at least partially resides within the barrel (including those that use a two-piece telescoping plunger) are often referred to as "compact" applicators because of their decreased overall length (i.e., the length of the applicator in a non-deployed configuration). In full size applicators, the overall length includes the applicator barrel and a single piece plunger that extends outwardly from the plunger end of the applicator, where a substantial portion of the plunger length is external to the applicator barrel. In compact applicators, the overall length includes the applicator barrel and the length of the two-piece plunger that extends outwardly from the plunger end of the applicator, where the length of the two-piece plunger extending outwardly is typically shorter than the unitary plungers common to full-size applicators, thereby providing a shorter overall length.

A person of skill in the art will recognize that there is a sizable market for tampon applicators having a reduced length (i.e. compact applicators) because they can be discretely stored and handled by a user. To achieve the desired shorter overall length, many currently available compact applicators have a barrel shorter in length than a full length barrel, but such decreased length is at least partly accomplished by decreasing the grip region of the applicator. Although the decreased length of a compact applicator is desirable because of the discreteness it provides, it is undesirable to provide an applicator with a grip region smaller than the grip region provided on a full length applicator; e.g., the shorter length grip region makes the product more difficult to use.

A person of skill in the art will also recognize that there is a further need to provide an improved insertion experience with compact applicators. Compact applicators achieve a reduced overall length by shortening, amongst other things, the length of the petals. There is a further need to improve the mechanics of compact applicators such that a longer and/or tapered insertion end and/or petals can be utilized in a compact applicator format.

A person of skill in the art will also recognize that there is further need for compact applicators having two piece plungers where such plungers require little force to assemble, provide discrete assurance via one or more sensorial indicators such as visual, tactile and/or audible feedback, that such assembly has been achieved correctly.

SUMMARY OF THE INVENTION

According to the present invention, a tampon applicator is provided that includes a barrel and a telescoping two-piece plunger. The barrel extends lengthwise between a plunger end and an insertion end. The barrel defines an interior cavity and includes a grip region, a transition region, a main body region, and an insertion end region. The transition region is disposed between the main body region and the grip region, and an insertion end region typically having petals is disposed between the insertion end and the main body region. The telescoping two-piece plunger includes an outer sleeve and an inner sleeve having a digit portion. The plunger is configured to selectively reside in a non-deployed configuration or a deployed configuration. For purposes of the present disclosure, "configuration" and "state" are interchangeable. In the non-deployed configuration substantially all the inner sleeve is disposed within the outer sleeve and substantially all the outer sleeve is disposed within the interior cavity of the barrel. In the deployed configuration substantially all the inner sleeve is disposed outside the outer sleeve.

According to another aspect of the present disclosure, a tampon applicator is provided that includes a tampon having a length, a barrel, and a telescoping two-piece plunger. The barrel extends lengthwise between a plunger end and an insertion end. The barrel includes a grip region, a transition region, a main body region, an insertion end region having a plurality of petals, and an interior cavity. The transition region is disposed between the main body region and the grip region, and the petals are disposed between the insertion end and the main body region. The telescoping two-piece plunger includes an outer sleeve and an inner sleeve. The inner sleeve has a stem portion with a length and a digit portion, and the length of the stem portion is substantially equal to the length of the tampon.

According to another aspect of the present disclosure, a tampon applicator is provided that includes a barrel and a telescoping two-piece plunger. The barrel defines an interior cavity and extends lengthwise between a plunger end and an insertion end. The barrel includes a grip region, a transition region, a main body region, and an insertion end region having a plurality of petals. The transition region is disposed between the main body region and the grip region, and the petals are disposed between the insertion end and the main body region. The telescoping two-piece plunger includes an outer sleeve and an inner sleeve. The sleeves are selectively actuable into a deployed configuration in which the inner and outer sleeves are combined into a unitary member. The inner sleeve has a stem portion with a length and a digit portion. In the deployed configuration, the plunger is selectively movable in a lengthwise direction relative to the barrel, for a full stroke travel, where a full stroke travel is substantially equal to the length of the inner sleeve stem portion.

According to yet another aspect of the present invention, the inner sleeve has an inner connection mechanism that assists in the selective actuation with the outer sleeve. The inner connection mechanism has a detent mechanism. In one embodiment, the detent mechanism has a flexible portion. As the inner sleeve is drawn outward from the outer sleeve, the flexible portion is deflected and thereafter released (i.e. after it passes over at least a portion of the mating feature on the outer sleeve) and creates a connection between the inner sleeve and the outer sleeve. The inner connection mechanism assists in the retention of a rearward flange or coupler of the outer sleeve, thereby ensuring a stable connection between the inner and outer sleeve.

According to a further aspect of the present invention, the outer sleeve has an outer connection mechanism. The outer connection mechanism has a detent mechanism. In one embodiment, the detent mechanism has a flexible portion that corresponds to an inner connection mechanism on the inner sleeve.

In some embodiments, the inner connection mechanism and/or the outer connection mechanism is a detent mechanism, a flange or a coupler.

In an initial state (i.e. prior to actuation), the outer connection mechanism at least partially retains the inner connection mechanism of the inner sleeve to ensure the two-piece plunger does not reach a deployed or partially deployed state prior to the intended time for use of the product.

According to a further aspect of the present invention, the outer sleeve and the inner sleeve each have features that assist with one or more components the assembly of tampon applicator assembly. The inner connection mechanism and outer connection mechanism assist with the assembly of one or more components of the tampon applicator assembly, such that (a) the outer sleeve is within the applicator barrel, (b) the outer sleeve is adjacent the tampon within the applicator barrel, and/or (c) the inner sleeve is telescoped within the outer sleeve. In other embodiments, the inner sleeve and outer sleeve are assembled in series where the outer sleeve is inserted through the insertion end of the applicator barrel, and the inner sleeve is thereafter inserted through the insertion end and telescoped within the outer sleeve. In this embodiment, the tampon is thereafter inserted through the insertion end. In another embodiment, the inner sleeve is assembled into the outer sleeve prior to insertion into the tampon applicator barrel.

The present method and advantages associated therewith will become more readily apparent in view of the detailed description provided below, including the accompanying drawings.

BRIEF DESCRIPTION OF THE DRAWINGS

FIG. 25 is an angled view of a present disclosure plunger embodiment, illustrating the plunger sleeves in a deployed configuration.

FIG. 26 is a diagrammatic sectional view of a present disclosure plunger embodiment, illustrating the plunger sleeves in a deployed configuration.

FIG. 27 is a diagrammatic sectional view of a present disclosure plunger embodiment, illustrating the plunger sleeves in a deployed configuration.

FIG. 30 is a diagrammatic view of a present disclosure applicator barrel embodiment.

FIG. 31 is a diagrammatic view of a present disclosure applicator barrel embodiment.

FIG. 32 is a diagrammatic view of a present disclosure applicator barrel embodiment.

FIG. 33 is a diagrammatic view of a present disclosure applicator barrel embodiment.

DETAILED DESCRIPTION

Figure 1:
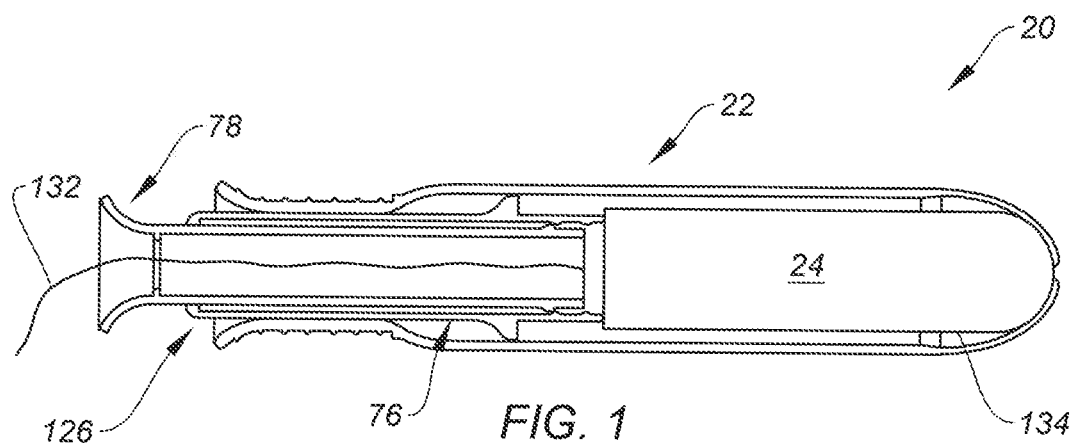
FIG. 1 is a sectioned diagrammatic view of a present disclosure tampon applicator embodiment with a two-piece plunger residing in a non-deployed position.
Figure 2:
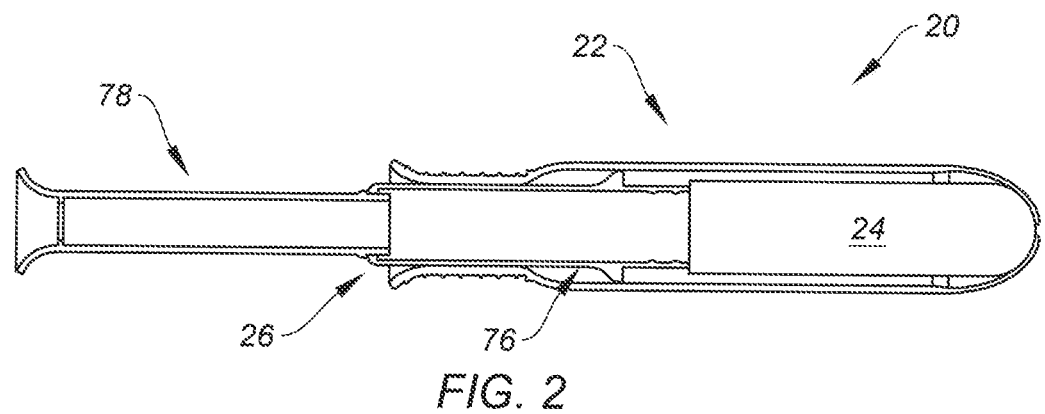
FIG. 2 is a sectioned diagrammatic view of a present disclosure tampon applicator embodiment with a two-piece plunger residing in a deployed position and a tampon disposed within the barrel of the applicator.
Figure 3:
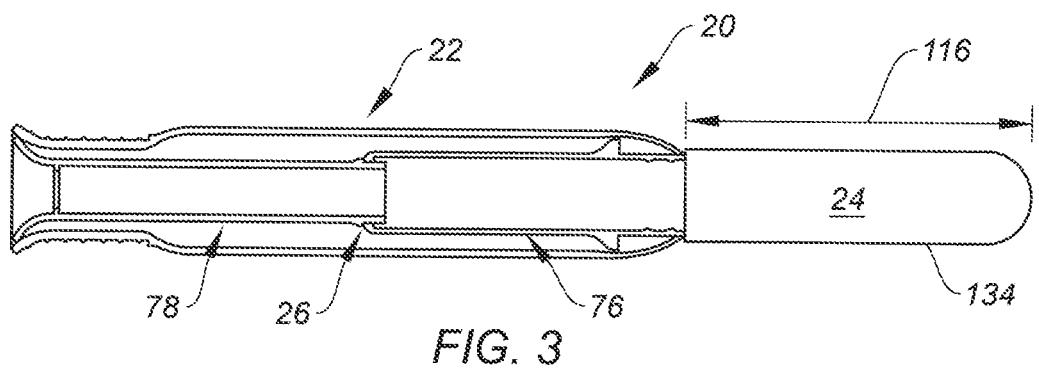
FIG. 3 is a sectioned diagrammatic view of a present disclosure tampon applicator embodiment with a two-piece plunger residing in a deployed position and a tampon expelled from the barrel of the applicator.

As shown by FIGS. 1-3, the tampon applicator 20 constructed according to the present invention comprises a barrel 22 operable to contain a tampon 24, and a telescoping two piece plunger 26. The two-piece plunger 26 is selectively positionable in a non-deployed configuration and in deployed configuration.

Figure 4:
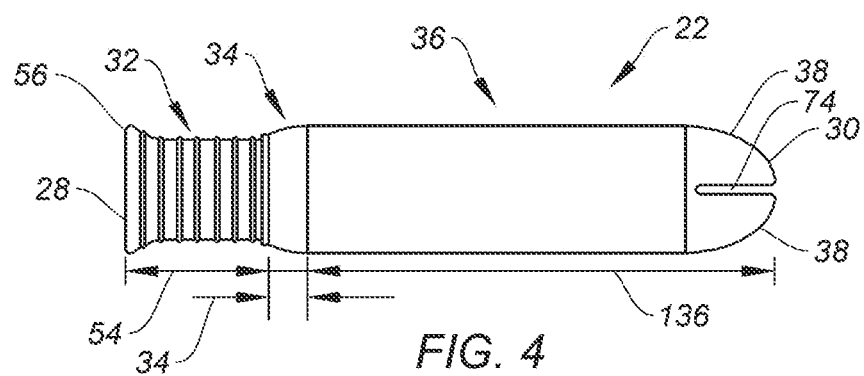
FIG. 4 is a diagrammatic view of a present disclosure tampon applicator barrel embodiment.
Figure 5:
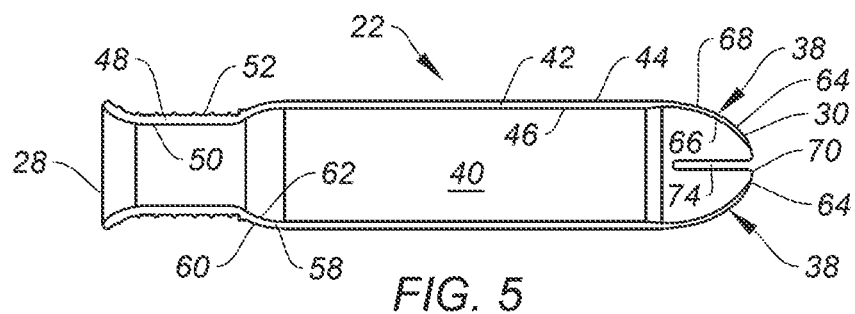
FIG. 5 is a sectional view of the barrel embodiment shown in FIG. 4.
Figure 6:
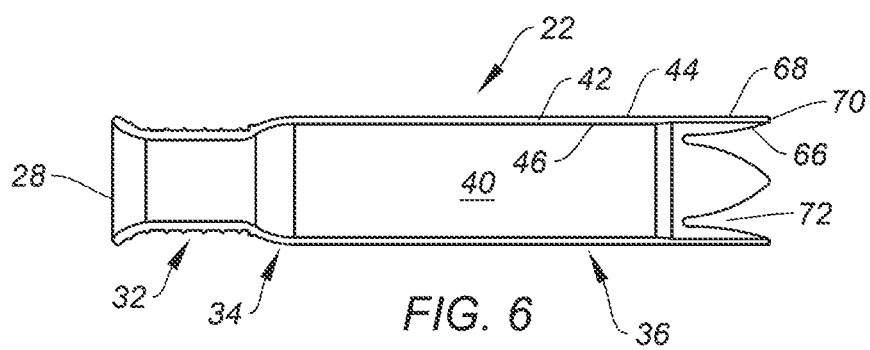
FIG. 6 is a sectional view of the barrel embodiment shown in FIG. 4, showing the petals extended outwardly.
Figure 7:
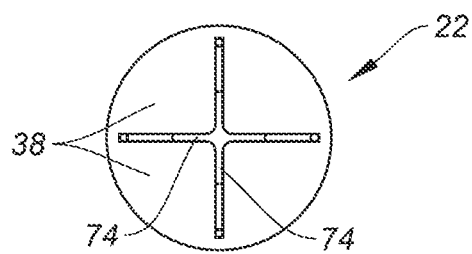
FIG. 7 is a diagrammatic end view of the barrel embodiment shown in FIG. 4.

Now referring to FIGS. 4 and 5, the barrel 22 has a length 136 that extends between a plunger end 28 and an insertion end 30. The barrel 22 includes a grip region 32, a transition region 34, a main body region 36, an insertion end region 37 having a plurality of petals 38, and an interior cavity 40 extending between the insertion end 30 and the plunger end 28. The transition region 34 has a length 135 and is disposed between the main body region 36 and the grip region 32. The petals 38 are disposed between the insertion end 30 and the main body region 36. The main body region 36 extends from the petals 38 to the transition region 34, and the grip region 32 extends from the plunger end 28 to the transition region 34.

In some embodiments, the main body region 36 is defined by a circumferentially extending main body wall 42 having an outer surface 44 disposed at a constant outer diameter and an inner surface 46 disposed at a constant inner diameter; e.g., the wall 42 has a generally constant thickness. The inner surface 46 having a constant inner diameter along the main body wall 42 can help create a consistent ejection of the tampon 24 into the user's body. In other words, the generally constant inner diameter helps avoid instances where the tampon 24 might wobble (i.e. if the tampon's 24 outer diameter is less than the inner diameter) as the unitary and deployed plunger 26 pushes the tampon 24 out of the barrel 22 of the applicator 20. The main body wall inner surface 46 defines a portion of the interior cavity 40 of the barrel 22. In some embodiments the main body region 36 is defined by a main body wall 42 having a tapered configuration with the outer surface 44 disposed at a first outer diameter adjacent the transition region 34 and disposed at a second outer diameter adjacent the insertion end 30 of the petals 38, with the first outer diameter greater than the second outer diameter; e.g., the main body region 36 decreasingly tapers in the direction from the transition region 34 the insertion end region 37 with petals 38, and/or decreasingly tapers in the direction opposite to the direction in which the transition region 34 tapers (i.e. the transition region 34 tapers towards the grip region 32). A barrel 22 that varies in external geometry (i.e. along the outer surface 44) can provide an improved user experience as the product is used (i.e. inserted and/or removed) from the user's body. FIGS. 4 and 5 illustrate a main body region 36 having a circular shaped cross-section. The present disclosure is not limited to a main body region 36 having a circular cross-sectional shape.

The grip region 32 is defined by a circumferentially extending grip wall 48 having an inner surface 50 disposed at a constant inner diameter and an outer surface 52. The grip wall inner surface 50 defines a portion of the interior cavity 40 of the barrel 22. The grip region 32 has a length 54 that extends between the plunger end 28 and the transition region 34, which length 54 is typical for a full length barrel 22. In some embodiments, the outer surface 52 of the grip wall 48 may have a constant outer diameter. In some embodiments, the grip wall outer surface 52 may include protrusions 130 that extend radially outwardly from the outer surface 52; e.g., to facilitate the user's grip of the device. In some embodiments, the grip region 32 may include an outwardly flared section 56 disposed at the plunger end 28; e.g., the outwardly flared section 56 may transition from the outer diameter of the grip region 32 to a second diameter contiguous with the plunger end 28, which second diameter is greater than the outer diameter of the grip region 32. The outer diameter 174 of the flared section 56 is at least about 0.050 inches greater than the diameter 170 of the recessed portion of the grip region 36, as demonstrated by reference numeral 166. Preferably, the outer diameter 174 of the flared section 56 is at least about 0.075 inches greater than the outer diameter 170 of the recessed portion of the grip region 36. More preferably, the outer diameter 174 of the flared section 56 is at least about 0.100 inches greater than the outer diameter 170 of the recessed portion of the grip region 36. In preferred embodiments, the length 54 of the grip region 32 is greater than 0.5 inches (12.7 mm). In other preferred embodiments the length 54 of the grip region 32 is also less than 0.8 inches (20.3 mm). In yet other preferred embodiments, the grip region 32 may have a varying inner diameter along the inner surface 50 and/or a varying outer diameter along the outer surface 52.

The transition region 34 is defined by a circumferentially extending transition wall 58 having an outer surface 60 and an inner surface 62. The transition wall inner surface 62 defines a portion of the interior cavity 40 of the barrel 22. The outer surface 60 is disposed at an outer diameter that changes from the grip region 32 to the main body region 36. For example, the outer diameter of the transition wall 58 at the interface with the grip region 32 may be equal to the outer diameter of the grip region outer surface 52, and may taper outwardly increasing in diameter in the direction of the main body region 36. At the interface with the main body region 36, the outer diameter of the transition wall 58 may equal the outer diameter of the main body region outer surface 44. The transition region 34 generally has a length 135 of about 0.100 inches to about 0.500 inches.

The plurality of petals 38 may be integrally attached to the main body region 36 of the barrel 22. In the embodiment shown in FIGS. 4-7, the plurality of petals 38 includes four petals 38. Each petal 38 comprises a petal wall 64 defined by an inner surface 66 and an outer surface 68, which petal wall terminates at a petal tip end 70. The inner surfaces 66 of the petals 38 define a portion of the interior cavity 40 of the barrel 22 when the petals are not deflected outwardly. A portion, or all, of each petal wall 64 may have a thickness (e.g., less than the main body wall thickness) that facilitates deflection of the petal 38 as will be described below. In embodiments such as those where the petals 38 are integrally attached to the main body region 36, prior to forming, an approximately V-shaped notch void 72 may be disposed between adjacent petals 38. After inserting the tampon 24 into the barrel 22, the petals 38 are formed inwardly to form an arcuate shape at the insertion end 30, such that a slot 74 (i.e. a break in the barrel wall forming a cut) is disposed between adjacent petals 38. As will be described below, the petals 38 form an enclosure at the insertion end 30 that encloses the tampon 24 within the interior cavity 40 of the barrel 22. The present disclosure is not limited to any particular number of petals 38, or any particular petal configuration. In other words, the applicator of the present disclosure could have two, three, four, five, six, seven, or eight or more petals 38, depending on a plurality of factors such as the desired Ejection Force of the tampon 24 and/or the column strength the unitary and deployed plunger 26 can provide. In some embodiments, the petals 38 and/or insertion end region 144 in general can have an elongate or tapered geometry thereby facilitating comfortable insertion. In some embodiments, the tampon 24 can have an insertion end 146 that has a complimentary tapered or elongate shape. Such shapes can include elliptical, hyperbolic and/or parabolic curves such that the curve is along the profile of the petals 38 or tampon insertion end 146.

The interior cavity 40 of the barrel 22, which extends between the insertion end 30 and the plunger end 28, is defined by the inner surfaces of the grip wall 48, the transition wall, the main body wall 42, and the petal walls 64.

Figure 12:
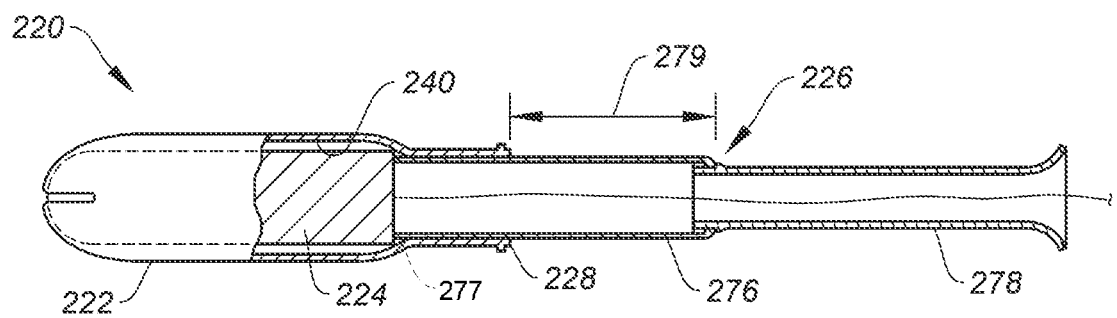
FIG. 12 illustrates a prior art tampon applicator.
Figures 13, 14, 15, 16:
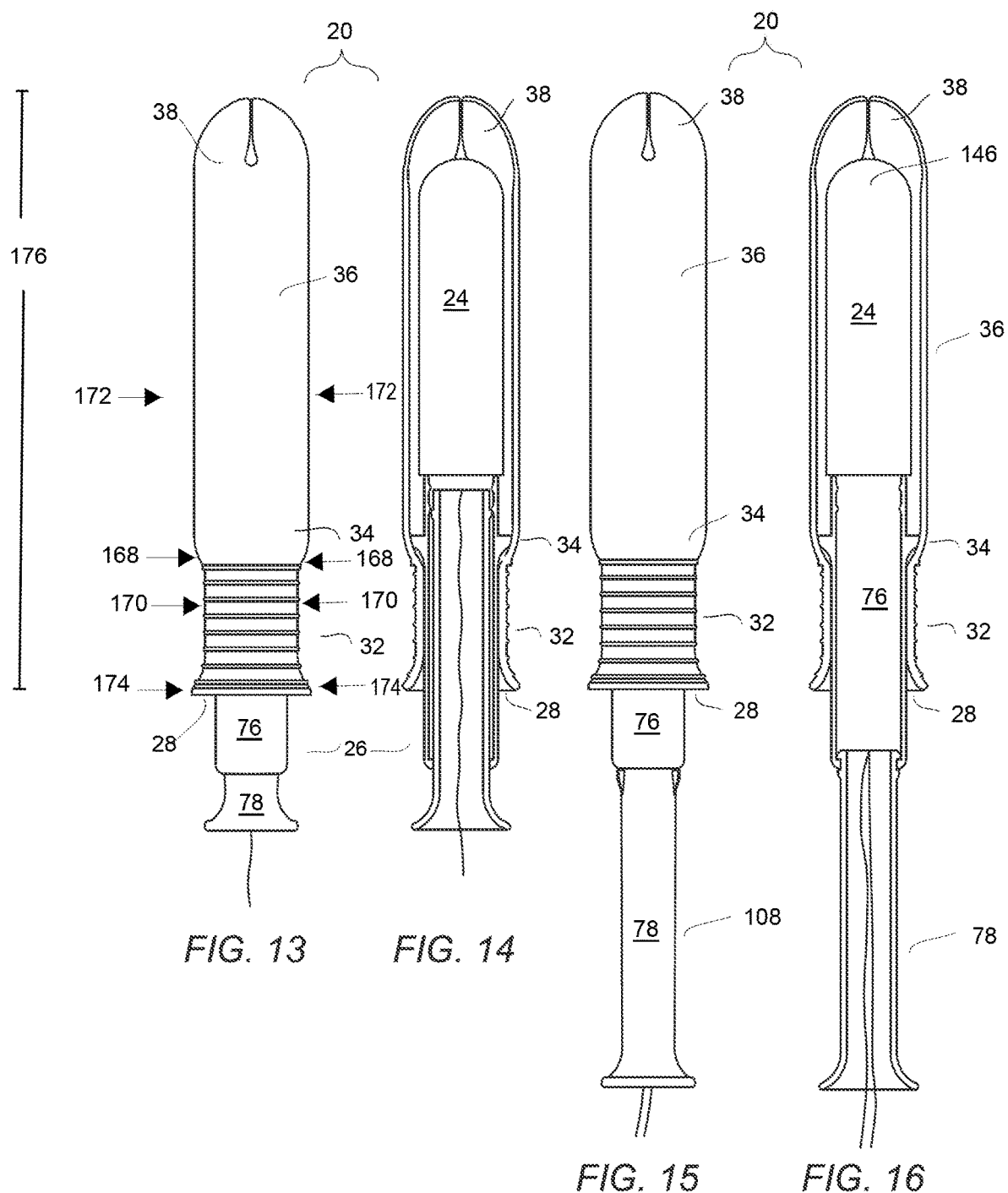
FIG. 13 is a diagrammatic view of a present disclosure tampon applicator embodiment with a two-piece plunger residing in a non-deployed position.
FIG. 14 is a sectioned diagrammatic view of a present disclosure tampon applicator embodiment with a two-piece plunger residing in a non-deployed position.
FIG. 15 is a diagrammatic view of a present disclosure tampon applicator embodiment with a two-piece plunger residing in a deployed position.
FIG. 16 is a sectioned diagrammatic view of a present disclosure tampon applicator embodiment with a two-piece plunger residing in deployed position.
Figure 17:
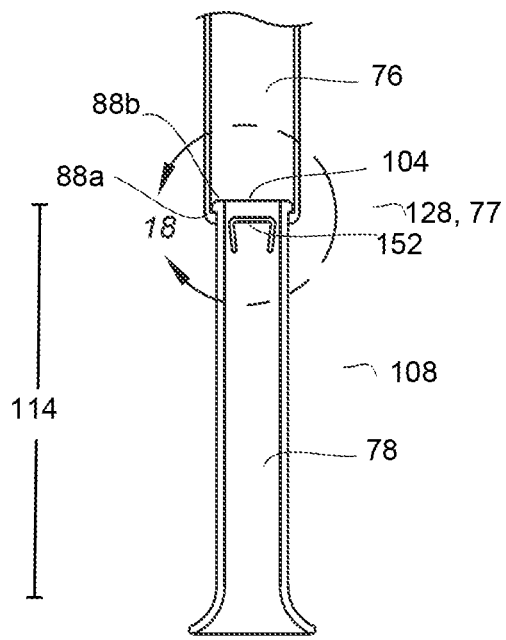
FIG. 17 is a diagrammatic view of a present disclosure plunger embodiment, illustrating the plunger sleeves in a deployed configuration.
Figure 18:
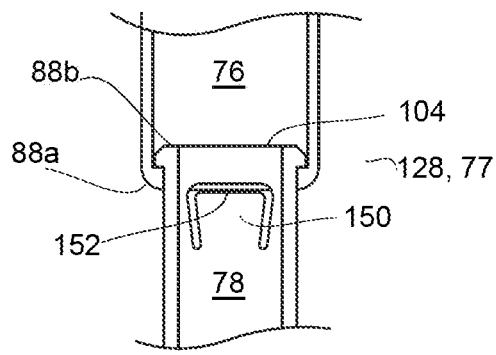
FIG. 18 is a diagrammatic sectional view of a present disclosure plunger embodiment, illustrating the plunger sleeves in a deployed configuration.
Figure 19:
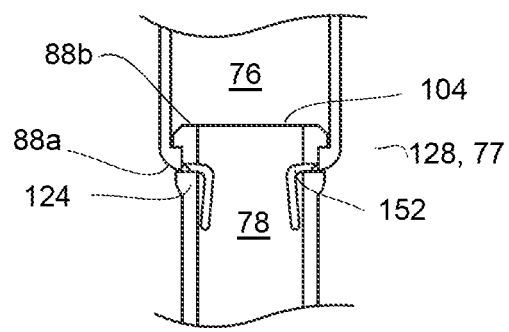
FIG. 19 is a diagrammatic sectional view of a present disclosure plunger embodiment, illustrating the plunger sleeves in a deployed configuration.
Figure 20:
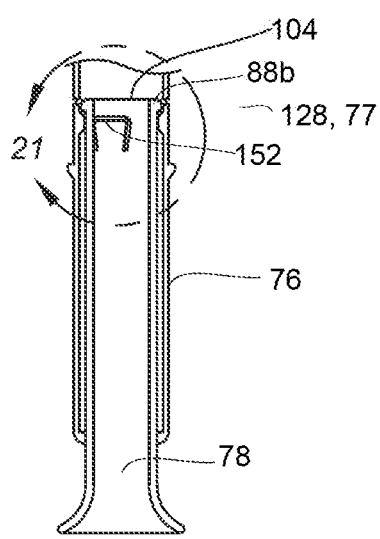
FIG. 20 is a diagrammatic view of a present disclosure plunger embodiment, illustrating the plunger sleeves in a non-deployed configuration.
Figure 21:
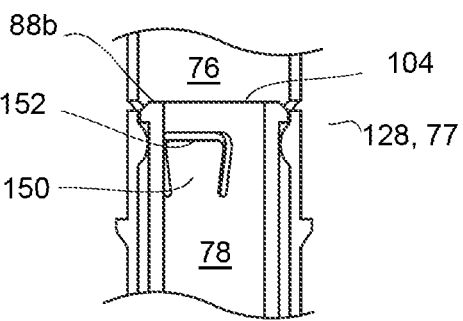
FIG. 21 is a diagrammatic sectional view of a present disclosure plunger embodiment, illustrating the plunger sleeves in a non-deployed configuration.

A person of skill in the art will recognize that there is a sizable market for tampon applicator having a reduced length; the reduced length facilitates discrete storage and handling of the applicator. Typical full length tampon applicators have a length in the range of 4.5 inches (11.4 cm) to 5.5 inches (13.9 cm), which length is defined in part by at least a portion of the plunger. Currently available reduced length tampon applicators (typically referred to as "compact") typically have a length in the range of 2.5 inches (6.35 cm) to 3.5 inches (8.89 cm), which is less than that of full length applicators. The length of the present barrel 22 is preferably less than three inches (76.2 mm) and more than 2.5" (63.5 mm). In many instances, currently available compact applicators have a barrel shorter in length than a full length barrel, but such decreased length is at least partly accomplished by decreasing the grip region of the applicator. For example, existing compact applicators have at least one of a shortened insertion end, barrel region, and grip region. It is believed existing compact applicators lack a transition region as described by the present disclosure. Although the decreased length of a compact applicator is desirable because of the discreteness it provides, it is undesirable to provide an applicator with a grip region smaller than that available on a full length applicator; e.g., the shorter length grip region makes the product more difficult to use. Furthermore, having a grip region 32 with an outer diameter 170 that is significantly less than the outer diameter 172 of the main body region 36 is advantageous in that it helps assist, by providing a surface on which a user can stabilize at least one of a user's fingers during preparation and insertion of the compact applicator 20. In one embodiment, the outer diameter 170 of the grip region 32 is at least about 0.050 inches smaller than the outer diameter 172 of the main body region 36 adjacent the transition region 34, as generally represented by reference numeral 168. Preferably, the outer diameter 170 of the recessed portion of the grip region 32 is at least about 0.075 inches less than the outer diameter 172 of the main body region 36 adjacent the transition region 34. More preferably, the outer diameter 170 of the grip region 32 is at least about 0.100 inches less than the outer diameter 172 of the main body region 36 adjacent the transition region 34. Prior art compact applicators 220, as represented by FIG. 12 lack such a recessed grip region, for reasons described throughout the present disclosure. The present tampon applicator 20, in contrast, provides a full length barrel 36, and in particular a grip region 32 having a length 54 typically associated with full length tampon applicators (and the advantages associated therewith), in an overall length typically associated with compact applicators.

FIGS. 30-33 are exemplary embodiments of applicators having various dimensions, all of which fall within the ranges of dimensions described throughout the present disclosure. One skilled in the art understands that the embodiments of FIGS. 30-33 demonstrate a variety of dimensions the compact applicator of the present disclosure provides, where such dimensions are similar to those of full-size applicators. As exemplified in FIG. 30, the overall barrel length 176 is about 2.9 inches, where the grip region 32 has a length 54 of about 0.8 inches, the main body region 36 has an outer diameter 172 adjacent the transition region 38 of about 0.47 inches, and a plunger end 28 outer diameter 174 of about 0.47 inches. The insertion end region 37 has elongated and tapered petals that fall within a Taper Ratio of about 0.3 to about 1.0. The "Taper Ratio" is defined as the radius 178 of the insertion end region 37 at the base of the petals 38 (i.e. where the cuts between each petal end/meet the main body region) divided by the length 180 of the insertion end region 37 (i.e. the petal tip ends 70 to the base 39 of the petals 38).

Referring now to FIG. 31, the overall barrel length 176 is also about 2.9 inches, the grip region 32 has a length 54 of about 0.5 inches, the outer diameter 172 of main body region 36 adjacent the adjacent the transition region 34 is about 0.6 inches, and the plunger end 28 outer diameter 174 is about 0.65 inches. The insertion end region 37, as with FIG. 30, also has an elongated and tapered geometry, where the taper ratio is about 0.3 to about 1.0.

Referring now to FIG. 32, the overall barrel length 176 is about 2.85 inches, the grip region 32 has a length 54 of about 0.6 inches, the outer diameter 172 of main body region 36 adjacent the transition region 34 is about 0.55 inches, and the plunger end 28 outer diameter 174 is about 0.57 inches.

Referring now to FIG. 33, the overall barrel length 176 is about 2.87 inches, the grip region 32 has a length 54 of about 0.55 inches, the outer diameter 172 of the main body region 36 adjacent the transition region 34 is about 0.55 inches, and the plunger end 28 outer diameter 174 is about 0.55 inches.

In yet further embodiments, the grip region 32 provides an enhanced gripping surface that comprises one or more protrusions 130 or tabs 122 such as ribs or other raised (or recessed) features, a recessed and/or an at least partially arcuate shape that compliments the shape of a user's finger, and/or other features assisting in improving grippability such as use of materials having a higher coefficient of friction (rubber, thermoplastic elastomers, blends of materials, amongst other materials) than typical applicator materials (plastics such as polyethylene and polypropylene). In particular, as described throughout the present disclosure, the ability to provide a recessed and/or an at least partially arcuate shaped grip region 32 that helps assist in retaining and/or aligning at least one of a user's fingers is unique to compact applicators and made possible by the configurations of the present disclosure.

Figure 8:
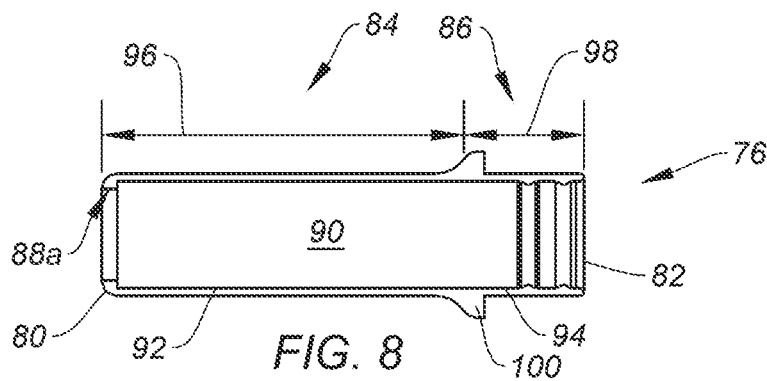
FIG. 8 is a diagrammatic sectional view of a present disclosure plunger outer sleeve embodiment.
Figure 9:
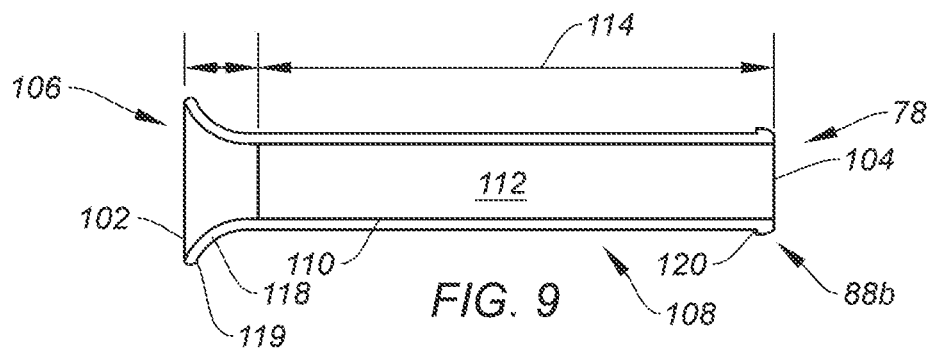
FIG. 9 is a diagrammatic sectional view of a present disclosure plunger inner sleeve embodiment.

Now referring to FIGS. 1-3, 8, and 9, the telescoping two piece plunger 26 includes an outer sleeve 76 (e.g. see FIG. 8) and an inner sleeve 78 (e.g. see FIG. 9). The outer sleeve 76 extends lengthwise between a coupling end 80 and an interior end 82. The outer sleeve 76 includes a first portion 84, a second portion 86, a coupler 88a, and an interior cavity 90. The first portion 84 is defined by a circumferentially extending wall 92 having an outer surface disposed at an outer diameter, and an inner surface 126 disposed at an inner diameter. The second portion 86 is defined by a circumferentially extending wall 94 having an outer surface disposed at an outer diameter, and an inner surface disposed at an inner diameter. The first portion 84 has a length 96 that extends between the coupling end 80 and the second portion 86, and the second portion 86 has a length 98 that extends between the interior end 82 and the first portion 84. The widths of the first and second portions 84, 86 are perpendicular to the lengths 96, 98.

The interior cavity 90 of the outer sleeve 76 is defined by the inner surfaces of the first and second portions 84, 86, which inner surfaces may have equal diameters. In the embodiment shown in FIG. 8, the interior cavity 90 extends between the coupling end 80 and the interior end 82, providing a passage completely through the outer sleeve 76. In alternative embodiments, the interior end 82 may be closed and the interior cavity 90 is therefore not accessible through the interior end 82.

In the embodiment shown in FIG. 8, both the first portion 84 and second portion 86 are shown having a circular shaped cross-section. The present disclosure is not limited to one or both of the first portion 84 and second portion 86 having a circular cross-sectional shape.

The outer sleeve 76 is configured so that the entire outer sleeve 76 cannot pass through the portion of the interior cavity 40 within the grip region 32. The first portion 84 of the outer sleeve 76 may be slidably received within the grip region 32 of the barrel 22, but the second portion 86 of the outer sleeve 76 cannot pass through the grip region 32 of the barrel 22 when moving the outer sleeve 76 in a direction from the insertion end 30 toward the plunger end 28 of the barrel 22. In other words, if an outer sleeve 76 is disposed within a main body region 36 of a barrel 22, the first portion 84 of the outer sleeve 76 can be slidably inserted into the interior cavity 40 within the grip region 32 (i.e. moving the outer sleeve 76 in a direction from the insertion end 30 toward the plunger end 28) but the second portion 86 of the outer sleeve 76 cannot pass through the grip region 32 of the barrel 22. To achieve the aforesaid movement limitations, the outer sleeve 76 may assume a number of different configurations. For example, the outer diameter of the second portion 86 may be greater than the outer diameter of the first portion 84 and greater than the inner diameter of the grip region 32. In this configuration, sufficient lengthwise movement of the outer sleeve 76 toward the plunger end 28 of the barrel 22 will result in the second portion 86 contacting the inner surface of the transition region 34, thereby preventing further lengthwise movement of the outer sleeve 76 in the same direction. As another example, the outer sleeve 76 may include a feature that extends radially outward at the intersection of the first portion 84 and the second portion 86. For example, the outer sleeve 76 may include a flange 100 (referred to hereinafter as a "stop flange 100") that extends radially outward from the outer surface of the second portion 86 or the first portion 84 at (or adjacent) the intersection of the first portion 84 and the second portion 86. The stop flange 100 extends a distance radially outward sufficient to prevent passage of the stop flange 100 and therefore the second portion 86, through the grip region 32 of the barrel 22. Consequently, sufficient lengthwise movement of the outer sleeve 76 toward the plunger end 28 of the barrel 22 will result in the stop flange 100 contacting the inner surface of the transition region 34, thereby preventing further lengthwise movement of the outer sleeve 76 in the same direction. The present disclosure is not limited to the above exemplary embodiments of the outer sleeve 76, and other outer sleeve 76 configurations wherein the first portion 84 of the outer sleeve 76 is slidably received within the grip region 32 of the barrel 22, and the second portion 86 of the outer sleeve 76 cannot pass through the grip region 32 of the barrel 22 are within the scope of the present disclosure.

The outer sleeve 76 configuration (e.g. the length of the first portion 84, the location of the intersection of the first and second portions 84, 86, the location of a stop flange 100, etc.) relative to the configuration of the grip region 32 and transition region 34 is such that none, or no more than about 0.7 inches (17.78 mm), of the first portion 84 of the outer sleeve 76 is exposed beyond the plunger end 28 of the barrel 22 when two-piece plunger 26 is in the non-deployed configuration and the outer sleeve interior end 82 is in contact with tampon 24 disposed within the barrel 22.

In some embodiments, the stop flange 100 has a face 138 that is sloped and corresponds to the slope of the transition region inside wall 140. The sloped face 138 can be arcuate, stepped, linear, or combinations thereof, and functions to assist in distributing any force the user exerts on the plunger and applicator as the plunger is deployed to a fully deployed configuration along the transition region inside wall 140. The sloped face 138 can also assist in maximizing usage of the inner cavity 40 such that (a) the tampon 24 can have a length 116 similar to that of known full-size applicator tampons, (b) the grip region 32 can have a greater length as less length of the barrel 22 is used to store the non-deployed plunger 26, and/or (c) the barrel 22 can have a greater length and/or a length more closely resembling full-size applicators and thereby providing an insertion depth of the tampon that is similar to full-size tampon applicators.

In some embodiments, the tampon 24 can have a reduced overall length to increase the flexibility in barrel design such that one or more full-size barrel components (or at the very least, one or more barrel components that have characteristics that more closely resemble full-size applicators than known compact applicators) can be utilized in a compact applicator form. Tampon 24 can be compressed radially and axially to be formed with a reduced length with respect to known tampons used with compact applicators. The tampon 24, despite having reduced length, achieves absorbency comparable to existing tampons in both full-size tampon applicator assemblies and compact applicator assemblies.

The coupler 88a of the outer sleeve 76, which is described further below, is disposed adjacent the coupling end 80 of the outer sleeve 76 and is operable to connect the outer sleeve 76 and inner sleeve 78 together into the deployed configuration via a connection mechanism 77. In some embodiments, the connection mechanism is an inner connection mechanism 79. In the deployed configuration the inner and outer sleeves 78, 76 are connected to one another thereby forming a unitary member. In the deployed configuration, the outer sleeve 76 and inner sleeve 78 are locked together in a manner that prevents relative lengthwise movement between the inner sleeve 78 and outer sleeve 76 during normal use of the applicator. Said another way, in the deployed configuration, outer sleeve 76 and inner sleeve 78 are locked together in a manner that prevents relative lengthwise movement between the inner sleeve 78 and outer sleeve 76 during normal use of the applicator such that an ejected tampon state can be obtained (i.e., where the tampon 24 is substantially outside the applicator 20 and can be retained within the user's body cavity when the consumer removes the applicator 20).

The inner sleeve 78 extends lengthwise between a contact end 102 and an interior end 104. The inner sleeve 78 includes a digit portion 106, a stem portion 108, and a coupler 88b. The stem portion 108 is defined by a circumferentially extending wall 110 having an outer surface disposed at an outer diameter, and an inner surface disposed at an inner diameter; i.e. the inner sleeve 78 has an interior cavity 112. Alternatively, the stem portion 108 may be a solid object with no interior cavity. The outer diameter of the stem portion 108 is less than the inner diameters of the first and second portions 84, 86 of the outer sleeve 76; e.g., a slide fit is formed between the outer sleeve 76 and the inner sleeve 78 that allows the inner sleeve 78 to be slidably received within the interior cavity 90 of the outer sleeve 76. As will be described below: a) the length 114 of the stem portion 108 of the inner sleeve 78 (i.e., the distance between the digit portion 106 and the interior end 104) is approximately equal to the length 116 of the tampon 24; and b) the length 114 of the stem portion 108 is substantially equal to a full stroke travel of the deployed plunger 26 adequate to expel a tampon 24 from the applicator barrel 22.

Further, in some embodiments, the length of the outer sleeve 76 and the length of the tampon 24 are generally equal to the length of the barrel 22. For instance, when the insertion end 146 of the tampon 24 is in contact with inner surface 66 of petals 38 at the insertion tip 144 of the applicator 20 and the outer sleeve 76 is adjacent and at least partially touching the tampon 24, the coupling end 80 will be generally near the plunger end 28.

In some embodiments, the length 116 of the tampon 24 may be slightly less than the length 114 of the stem portion 108 of the inner sleeve (e.g., in some embodiments the length 116 of the tampon is approximately 1.5 inches and the length 108 of the stem portion 108 of the inner sleeve 78 is approximately 1.6 inches). The full stroke travel of the deployed plunger 26 is defined as the lengthwise movement of the deployed plunger 26 relative to the barrel 22 of the applicator 20 between a first position where the plunger outer sleeve interior end 82 contacts the tampon 24 while the tampon 24 is completely disposed within the barrel 22 (as shown in FIG. 2), to a second position where the interior end 82 is substantially aligned with the petal tip ends, at which point the tampon 24 is expelled (as shown in FIG. 3).

The digit portion 106 of the inner sleeve 78 may be defined by a circumferentially extending wall 118 having an outer surface 119 disposed at an outer diameter and an inner surface. The digit portion has a length 115 spanning from the inner sleeve contact end 102 to the stem portion 108. The outer diameter of the digit portion 106 is typically greater than the inner diameter of the first portion 84 of the outer sleeve 76 to prevent the digit portion 106 from entering the interior cavity 90 of the outer sleeve 76. A digit portion 106 having an outer diameter greater than the inner diameter of the first portion 84 also facilitates use of the plunger 26; i.e. the larger diameter provides a surface that can be pulled on by the user's digits when deploying the plunger 26, and a second surface that can be pushed against by a user's digit(s) when expelling a tampon 24. The present disclosure is not limited to the digit portion 106 embodiment shown in FIG. 9. In the embodiment shown in FIG. 9, both the stein portion 108 and the digit portion 106 of the inner sleeve 78 are shown having a circular shaped cross-section. The present disclosure is not limited to one or both of the digit portion 106 and the stein portion 108 having a circular cross-sectional shape.

Figure 10A:
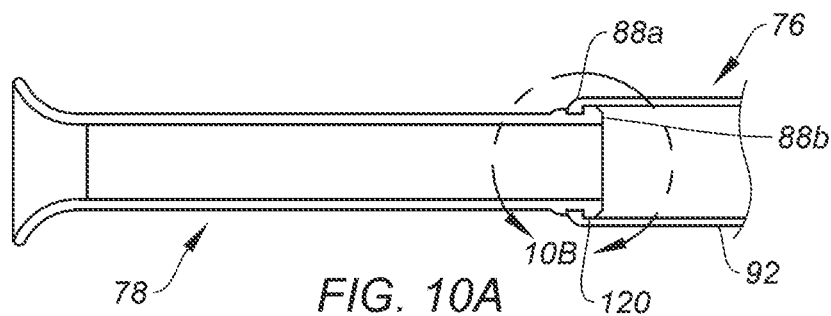
FIG. 10A is a diagrammatic sectional view of a present disclosure plunger embodiment, illustrating the plunger sleeves in a deployed configuration.
Figure 10B:
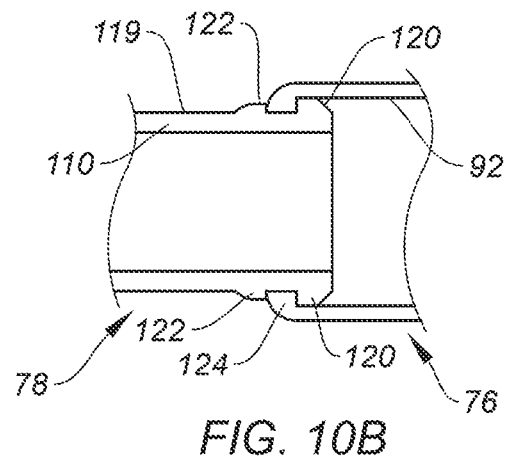
FIG. 10B is an enlarged view of a portion of FIG. 10A, illustrating a sleeve coupler embodiment.
Figure 11:
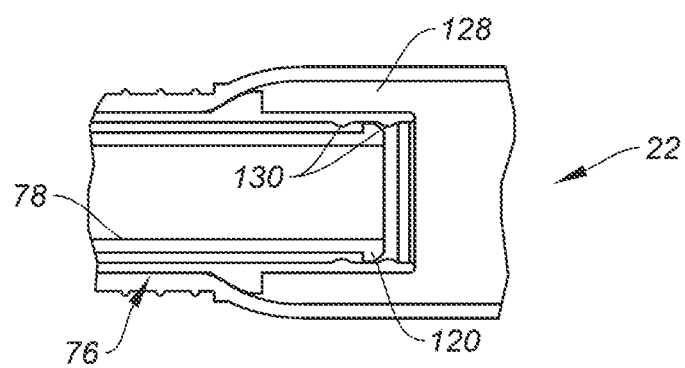
FIG. 11 is an enlarged view of a portion of FIG. 1, illustrating a detent embodiment.

The coupler 88b of the inner sleeve 78 is disposed adjacent the interior end of the inner sleeve 78. The couplers 88a, 88b of the inner sleeve 78 and outer sleeve 76 are configured to cooperate with one another to connect the outer sleeve 76 and inner sleeve 78 together into the plunger deployed configuration (see FIGS. 10A. 10B); e.g., mating male and female features that cooperate to lock the outer and inner sleeve 78 together. In the deployed configuration, the sleeves 76, 78 are locked together in a lengthwise extended configuration, and there is no relative lengthwise movement between the sleeves 76, 78 under normal operating conditions. The inner and outer sleeves 78, 76 locked in the deployed configuration form a unitary member. For example, as can be seen in FIGS. 10A and 10B, the coupler 88b of the inner sleeve 78 may include a flange 120 (or flange segments) and one or more tabs 122. The flange 120 (or flange segments) extends radially outward from the outer surface 119 of the stem portion, and circumferentially around at least a portion of the circumference of the stem portion 108. The one or more tabs 122 are spaced apart from the flange 120 a lengthwise distance and extend radially outwardly from the inner sleeve outer surface 119. The coupler 88a of the outer sleeve 76 may include a flange 124 (or flange segments) that extends radially inward from the inner surface 126 of the first portion 84 of the outer sleeve 76, and circumferentially around at least a portion of the circumference of the outer sleeve first portion 84. As will be described below, the couplers 88a, 88b of the inner and outer sleeves 78, 76 can be engaged with one another by sliding the inner sleeve 78 lengthwise relative to the outer sleeve 76 (i.e. pulling the inner sleeve 78 lengthwise out of the outer sleeve 76). If an adequate pull force is applied, one of the inner sleeve 78 or outer sleeve 76 will deform and the inwardly facing flange 124 of the outer sleeve 76 will be captured between the outwardly facing flange of the inner sleeve 78 and the one or more tabs 122, thereby locking the inner and outer sleeves 78, 76 in the deployed configuration. In this deployed configuration, the sleeves 76, 78 form a unitary member and relative lengthwise movement between the sleeves 76, 78 is prevented by the couplers 88a, 88b. The above described embodiment of the couplers 88a, 88b of the inner and outer sleeves 78, 76 are examples of acceptable mechanisms for locking the inner and outer sleeves 78, 76 together in the deployed configuration. The present disclosure is not limited to this example.

Now referring to FIGS. 1, 2, 8, 9, and 11, in some embodiments the inner and outer sleeves 78, 76 may collectively include a detent mechanism 128 (e.g., male and female mating components, such as flange 120 and protrusions 130). The detent mechanism 128 is operable to hold the outer sleeve 76 and inner sleeve 78 together (e.g. to prevent relative lengthwise movement between the sleeves) when the two piece plunger 26 is in the non-deployed configuration; i.e. when the inner sleeve 78 is substantially received within the outer sleeve 76. A lengthwise applied force can be used to overcome the detent mechanism 128 to permit relative lengthwise movement of the inner and outer sleeves 78, 76; i.e. so that the sleeves 76, 78 can be disposed in the deployed configuration. The detent mechanism 128 of the inner and outer sleeves 78, 76 is operable to positionally maintain the inner sleeve 78 relative to the outer sleeve 76 such that only the flared portion of the inner sleeve 78 is exposed outside of the outer sleeve 76 when the plunger 26 is in the non-deployed configuration. The present disclosure is not limited to this example.

Figure 22:
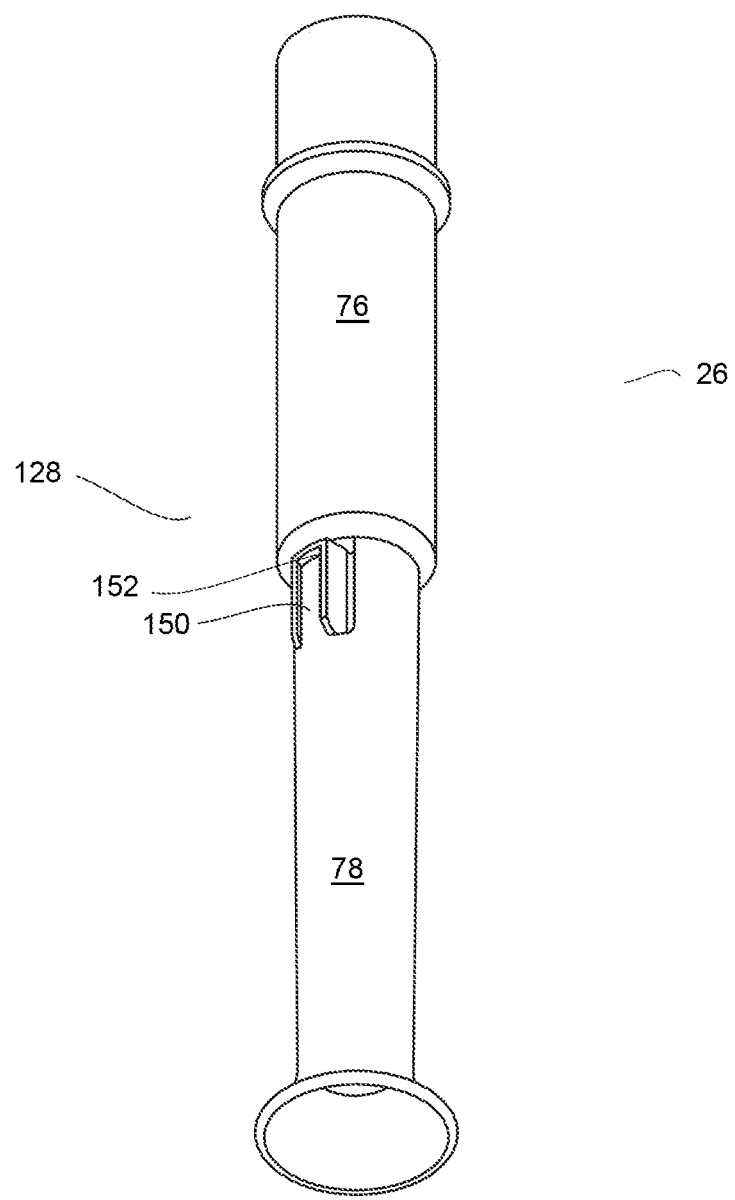
FIG. 22 is an angled view of a present disclosure plunger embodiment, illustrating the plunger sleeves in a deployed configuration.

Referring to FIGS. 13-27, in some embodiments, the detent mechanism 128 can further comprise a flexible latch 150. The flexible latch 150 has a free end 152 and can be peninsular in shape and permit inward deflection to assist in assembling the inner sleeve 78 and outer sleeve 76 in a deployed configuration. Once assembled and ready for use, as the inner sleeve 78 is drawn rearward and/or outward of outer sleeve 76, the flexible latch 150 deflects inwardly past flange 124. The flexible latch 150 can have its free end 152 positioned along the length 114 of stem portion 108 towards the interior end 104 and rearward of coupler(s) 88b. When positioned in this configuration the flexible tab 150 is deflected more easily and less susceptible to being caught or shearing during assembly into a deployed configuration, as flange 124 engages flange 124 on the non-free end 154 of flex-latch 150 and assists in deflecting the flex latch. It is possible to orient the flex latch 150 in the opposite direction (i.e. against the grain) such that the free-end 152 engages flange 124 first, In some embodiments, the flex latch 150 can be more arcuate in shape, as shown in FIGS. 17-21, or can be generally rectangular as shown in FIG. 22. One skilled in the art realizes other shapes and/or combinations of shapes are possible and within the scope of the present disclosure.

Figure 23:
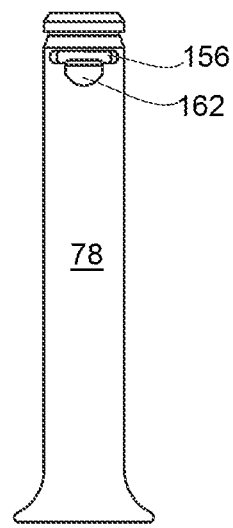
FIG. 23 is a diagrammatic view of a present disclosure plunger embodiment, illustrating the inner sleeve.
Figure 24:
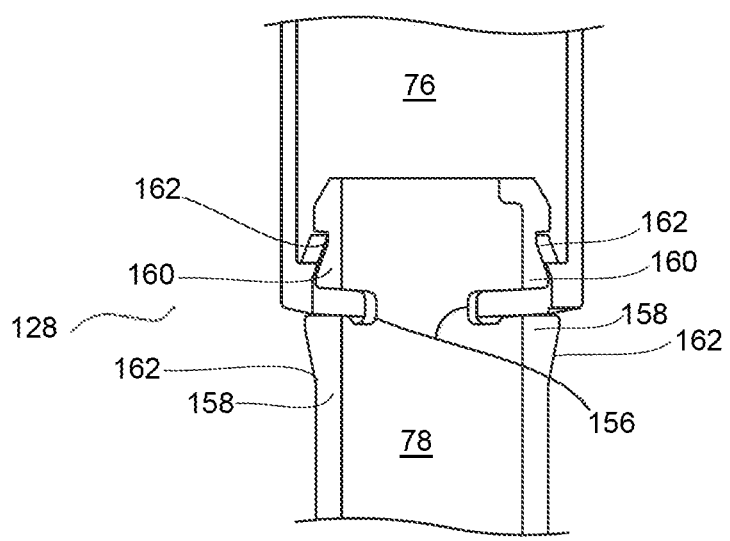
FIG. 24 is a diagrammatic sectional view of a present disclosure plunger embodiment, illustrating the plunger sleeves in a deployed configuration.

Referring to FIGS. 23-24, the detent mechanism 128 can comprise a gap 156. While FIGS. 23-24 demonstrate an embodiment where the gap 156 is generally slot-shaped, the gap 156 can be a variety of shapes and sizes. Inner plunger 78 has thickened regions 158 and 160 adjacent gap 156 to (a) assist in deflecting these surfaces during assembly of the inner sleeve 78 and outer sleeve 76 into a deployed configuration and (b) assist in retaining the inner sleeve 78 and outer sleeve 76 in the deployed configuration. Thickened regions 158 and 160 can be various shapes and sizes, and can provide ramped surfaces 162 to assist in (a) assembly and (b) retaining the assembly in a deployed configuration.

Referring now to FIGS. 25-27, the detent mechanism 128 enables a twist assembly to achieve a deployed configuration between the inner sleeve 78 and outer sleeve 76. The detent mechanism 128 is asymmetric about the perimeter of the inner sleeve 78 and thereby enables the inner sleeve 78 to be rotated with respect to the outer sleeve 76 and achieve a deployed configuration. In some embodiments, the detent mechanism 128 may comprise helical threads, thread segments, and/or a bayonet-style connection mechanism. The detent mechanism 128 may further include ramped surfaces 162 to assist in achieving a deployed configuration. In yet further embodiments, the detent mechanism 128 is flexible such that the detent mechanism 128 will be overcome by force along the length of the inner sleeve 78 with respect to the outer sleeve 76 and enable connection or detachment of the inner sleeve 78 and outer sleeve 76.

Referring to FIGS. 13-21, the outer sleeve 76 also comprises a detent mechanism 128. In one embodiment, the detent mechanism 128 is a flex latch 150. The flex latch 150 assists in assembling the inner sleeve 78 and outer sleeve during production by (a) exerting a slight force on at least one of the outer wall of stem portion 108, coupler(s) 88b, and flange 120, thereby causing the inner plunger 78 to be retained within the outer plunger 76, or (b) deflecting flange 120 such that flange 120 is retained by flex latch 150. As will be discussed below, the retention feature is critical not only for assembly processes where the two-piece plunger is assembled prior to assembling the remaining tampon applicator components, but is also critical in being unnoticeable to the consumer as the consumer begins to draw the inner plunger 78 rearward and/or outward from the outer plunger 76 to achieve a deployed configuration. In other words, the Retention Force, as further defined below, must be strong enough to maintain the inner sleeve 78 and outer sleeve 76 in an assembled condition for production purposes, and the force to overcome the connection mechanism 77 (having retention features) must be low enough to be unnoticeable to the consumer when the consumer prepares the applicator for use.

Figures 28, 29:
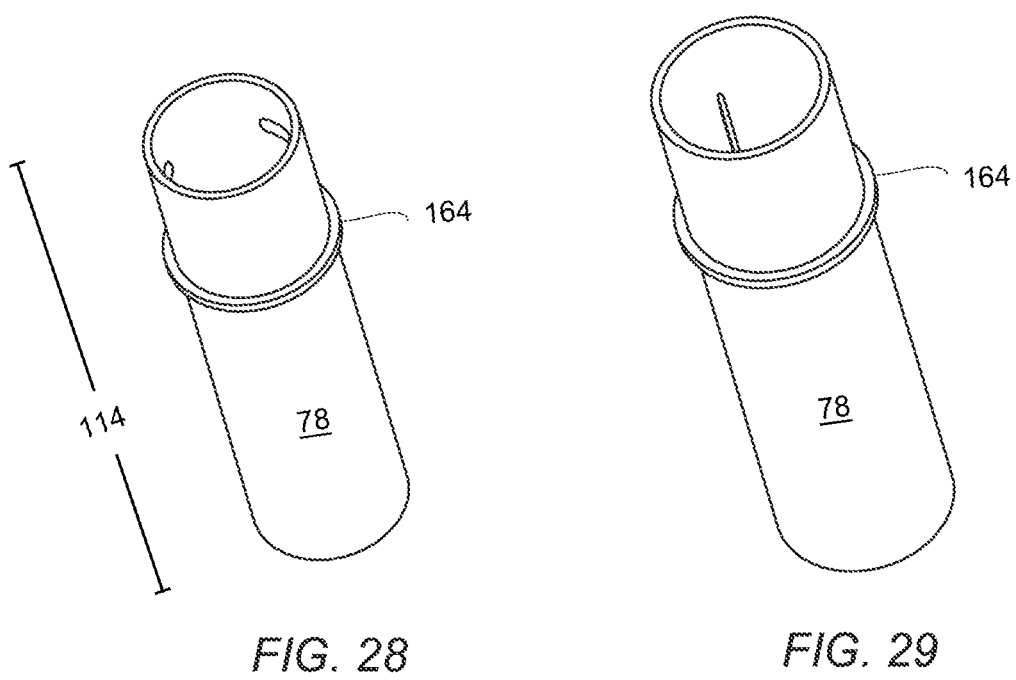
FIG. 28 is an angled view of a present disclosure plunger embodiment, illustrating the outer sleeve.
FIG. 29 is an angled view of a present disclosure plunger embodiment, illustrating the outer sleeve.

Referring to FIGS. 28 and 29, protrusions 164 may be used to assist in retaining the inner plunger 78 within the outer plunger 76 during production. The protrusions 164 can be various shapes and sizes, such as ribs, and the ribs can be in various alignment and frequency. As shown in FIG. 28, protrusions 164 can be positioned radially and such that their lengths are along the perimeter of a cross-sectional slice of inner plunger 78. As shown in FIG. 29, protrusions 164 can be positioned radially and such that their lengths are along the length 114 of inner plunger 78 (i.e. perpendicular to the perimeter of a cross-sectional slice of inner plunger 78). Protrusions 164 can be positioned along the length of outer sleeve 76 but are preferably positioned such that they align with flange 120 so at least one end of inner sleeve 78 is aligned with one end of outer sleeve 76. To our knowledge, prior art compact tampon applicators 220 that utilize a two piece telescoping plunger 226 are configured such that only a limited portion of the outer sleeve 276 (i.e. a flange portion 277—see prior art FIG. 12) resides within the same region of the barrel interior cavity 240 as the tampon 224 and the remainder of the interior cavity 240 of the barrel 222 is occupied by the 224 tampon. However, the coupled inner and outer sleeves 276, 278 of the plunger 222 (i.e., when the plunger is in a deployed configuration) must have a combined length great enough to ensure the tampon can be expelled during use via a full stroke of the plunger. To provide the necessary plunger full stroke length (i.e. the lengthwise movement of the deployed plunger relative to the barrel of the applicator necessary to expel the tampon) all prior art compact tampon applicators of which we are aware typically include a substantial portion 279 of the outer sleeve 276 extending out from the plunger end 228 of the barrel 222 when the two-piece plunger 226 is in the non-deployed configuration, and the outer sleeve 276 is in contact with the tampon disposed within the applicator barrel. As a result, the overall length of currently available compact tampon applicators of which we are aware is defined by the combined length of the barrel and the portion of the outer sleeve extending outwardly from the barrel when the two-piece plunger is in the non-deployed configuration.

Now referring to FIGS. 1-3, the present tampon applicator 20 is designed for use (and typically provided) with a sanitary tampon 24. The tampon 24 typically includes a pull-cord 132 attached to a body 134 of absorbent material. The pull cord 132 is one or more strands and in some embodiments is braided. The tampon 24 has a length 136 (i.e. the length of the body 134) that allows it to be disposed within the interior cavity 40 of the barrel 22 between the interior end 82 of the outer sleeve 76 of the plunger 26 and the petals 38 disposed at the insertion end 30 of the barrel 22. As indicated above, the length 136 of the present disclosure barrel 22 (from plunger end 28 to insertion end 30) is preferably less than three inches (76.2 mm). In preferred embodiments of the present disclosure, the length 116 of the tampon 24 is not greater than about 2 inches (50.8 mm). The tampon 24 of the present disclosure in this preferred embodiment having a length 116 that is not greater than about 2 inches permits the use of an applicator 20 having a barrel main body region 36 with a relatively shorter length and a grip region 32 with a relatively longer length 54 while still providing a compact applicator that has an overall length that is shorter than prior art full-size applicators, and substantially the same length or shorter than prior art compact applicators. The tampon of the present disclosure in the aforementioned preferred embodiment also permits the use of an applicator 22 having longer petals 38 or a longer insertion end region 37 while having an overall length that is substantially the same length or shorter than prior art compact applicators. The tampon of the present disclosure in the aforementioned preferred embodiment also permits the use of an applicator 22 similar in size to a full-size applicator with similar barrel main body region 36 and grip region 32 lengths, with an overall length that is substantially the same length or shorter than prior art compact applicators. In preferred embodiments, the length 136 of the tampon 24 is approximately equal to the length of the stein portion 108 of the inner sleeve 78 of the two-piece plunger 26. The configuration of the two-piece plunger 26 and barrel 22 described above, and the relatively short length 136 of the tampon 24, provide a compact applicator where the length of the outer sleeve 76 extending out from the barrel is substantially less than that found in prior art configurations; i.e. the exposed length of the outer sleeve in prior art applicators is substantially greater than any amount of outer sleeve 76 that may extend out from the barrel 22 in the present applicator 20. The aforesaid length of the present applicator 20 greatly increases the discreteness of the applicator while also, for example, improving and/or enlarging the length 54 of the grip region 32, thereby providing an easier product for the consumer to hold, assemble into a deployed state and thereafter insert and remove the applicator 20 from the user's body, and therefore the commercial desirability of the applicator 20. This is an improvement over currently existing compact applicators that compromise the length of the applicator and more specifically the length of the grip region in order to achieve a discrete product.

In the operation of the present tampon applicator 20, the applicator 20 is initially provided in the non-deployed configuration, wherein a tampon 24 is disposed within the interior cavity 40 of the main region of the barrel 22 and the two-piece plunger 26 is collapsed into the non-deployed configuration. Referring to FIG. 1, in the non-deployed configuration, no more than about 0.7 inches (17.78 mm) of the first portion 84 of the outer sleeve 76 is exposed beyond the plunger end 28 of the barrel 22 when the interior end 82 of the outer sleeve 76 is in contact with the tampon 24 disposed within the barrel 22.

Prior to use of the applicator 20, the user pulls the inner sleeve 78 portion of the two-piece plunger 26 lengthwise out of the outer sleeve 76. In those embodiments that include a detent mechanism 128 (for holding the sleeves 76, 78 in the non-deployed configuration), the user applies a force that is adequate to overcome the detent holding force. The inner sleeve 78 is subsequently drawn lengthwise outwardly relative to the outer sleeve 76 until the couplers 88a, 88b of the inner and outer sleeves 78, 76 engage one another and thereby lock the inner and outer sleeves 78, 76 together into a unitary member; i.e. the couplers 88a, 88b prevent relative lengthwise movement between the inner and outer sleeves 78, 76 during normal use of the applicator 20. When the sleeves 76, 78 are locked together, the two-piece plunger 26 is in the deployed configuration (e.g., see FIGS. 2 and 3).

Referring to FIGS. 2 and 3, to expel the tampon 24 from the applicator, the two-piece plunger 26 (with the inner and outer sleeves 78, 76 locked in the deployed configuration) is forced lengthwise a distance in a direction from the barrel plunger end 28 toward the insertion end 30. As the tampon 24 contacts the petals 38, the petals 38 deflect outwardly creating an aperture through which the tampon 24 may pass. As indicated above, the lengthwise distance traveled by the plunger 26 adequate to expel the tampon 24 is referred to as the full stroke travel of the plunger 26, which is defined as the lengthwise movement of the deployed plunger 26 relative to the barrel 22 of the applicator between a first position where the plunger outer sleeve interior end 82 contacts the tampon 24 while the tampon 24 is completely disposed within the barrel 22 (e.g. as shown in FIG. 2), to a second position where, at which point the tampon 24 is expelled (e.g. as shown in FIG. 3). At the point where the tampon 24 is fully expelled from the barrel 22, the interior end 82 of the outer sleeve 76 is substantially aligned with the petal tip ends 70 (see FIG. 3). In preferred embodiments of the present applicator 20, the full stroke travel of the plunger 26 is substantially equal to the length 114 of the stem portion 108 of the inner sleeve 78 of the plunger 26.

Figure 34:
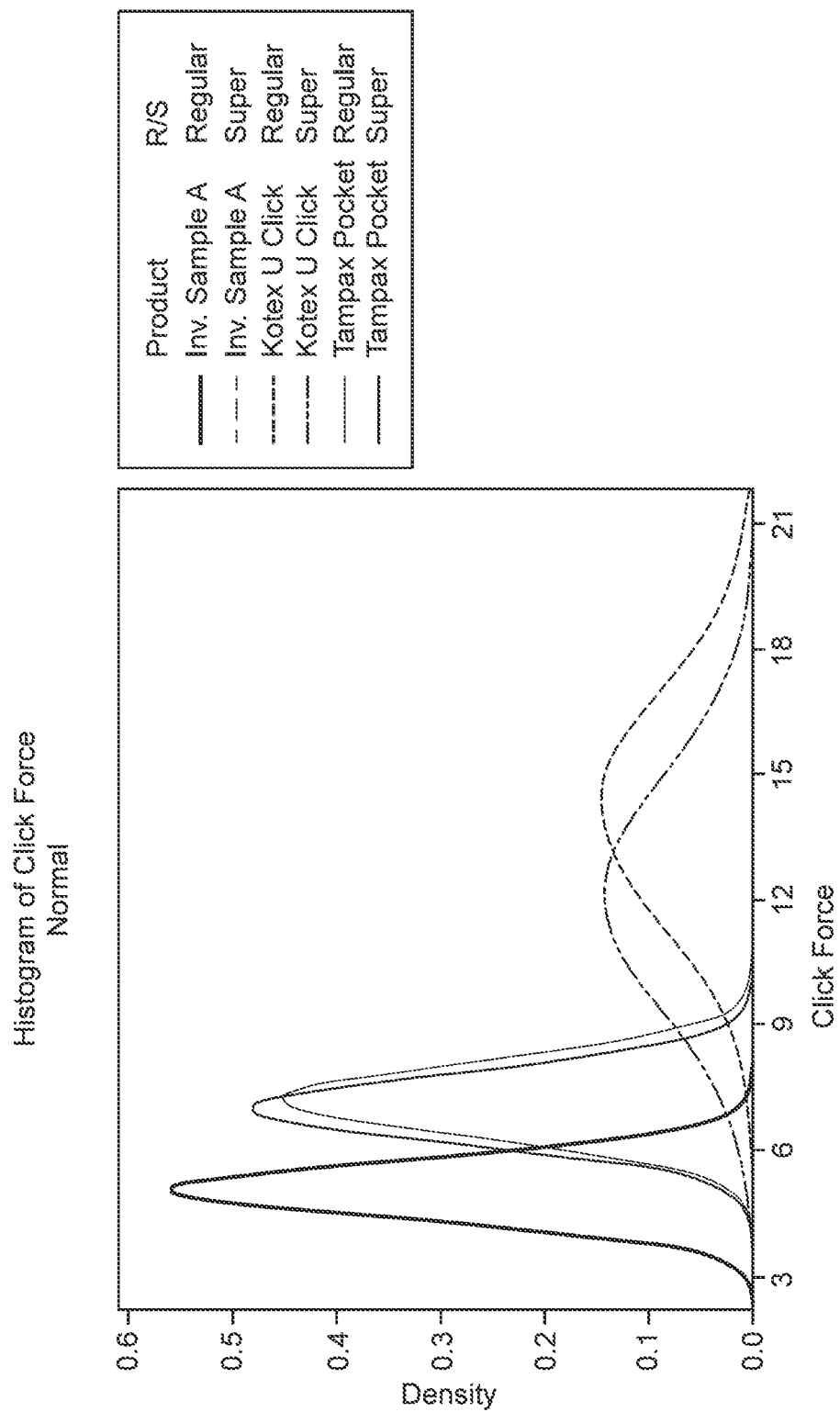
FIG. 34 is a histogram chart showing Click Force data for a tampon applicator of the present disclosure and prior art tampon applicators.

Referring to FIG. 34, the compact applicator 20 of the present disclosure is further advantageous in that it requires less force to assemble the inner sleeve 78 and outer sleeve 76 to achieve a deployed configuration. The so-called "Click Force" needs to be high enough to confirm a deployed configuration has been achieved, but low enough such that it is not overly burdensome to achieve a deployed configuration. Click Force is described as amount of force required to lock inner plunger 78 inside the outer plunger 76. FIG. 34 provides a Histogram of Click Force, demonstrating such Click Forces of Inventive Sample A, with respect to the U branded compact applicator by KOTEX ("Kotex U Click") and the POCKET PEARL branded compact applicator by TAMPAX ("Tampax Pocket"). Sample sizes of 88 for Inventive Sample A, 68 for Kotex U Click, and 71 for Tampax Pocket. As shown, the Inventive Sample A achieved the lowest median Click Force (illustrated as "density", i.e., the repeatability with which the Click Force value was achieved). Inventive Sample A achieved a Click Force of between about 3 and 7 N, with a mean Click Force of about 5 N, and a standard deviation of about 0.7N, while Kotex U Click achieved an average Click Force of about 7.5 N, and Tampax Pocket Achieved an average Click Force of about 13 N. Preferably, the Click Force is less than 13 N. More preferably, the Click Force is between about 3N to 7.5 N, and more preferably, between about 4 and 6 N.

The Click Force and Collapse Force (as described below) can be determined using a scale such as an Instron Model 5944 or equivalent machine, and by following this procedure. (Note: the Click Force is established in step 9a, and the Collapse Force is established in step 9b):

Procedure: Click Force and Collapse Force
1. Install the 100 N load cell on the Instron and calibrate.
2. Install the plunger assembly holder at the bottom jaw. The plunger assembly holder includes a fixture having two lateral bores to receive two screws that retain the fixture to the Instron Model 5944. The fixture has a middle orifice sized to receive the outer plunger.
3. If not already done, assemble inner plunger into the outer plunger. Place the assembly inside the middle orifice of the fixture. Tighten the 2 screws to secure the outer plunger between the top and bottom plates.
4. Insert a gage pin at the end of the inner plunger.
5. Install a 3-jaw chuck grip at the top jaw.
6. Lower down the upper jaw until the 3-jaw chuck grip is close to the end of the plunger assembly.
7. Close the 3-jaw chuck grip until you hear it "click" to make sure the chuck grip is securely grasping the end of the inner plunger/gage pin assembly
8. Zero out the force and extension.

9. Run the "Click Collapse Plunger Assembly" Test.

9a. The upper jaw will move with a speed of 200 mm/min until the inner plunger locks into the outer plunger and a "click" is detected.

9b. Once the "click" has been detected, the upper jaw will reverse direction (will move down) with a speed of 200 mm/min and push the inner plunger inside the outer plunger until the measured extension is "0".

Figure 35:
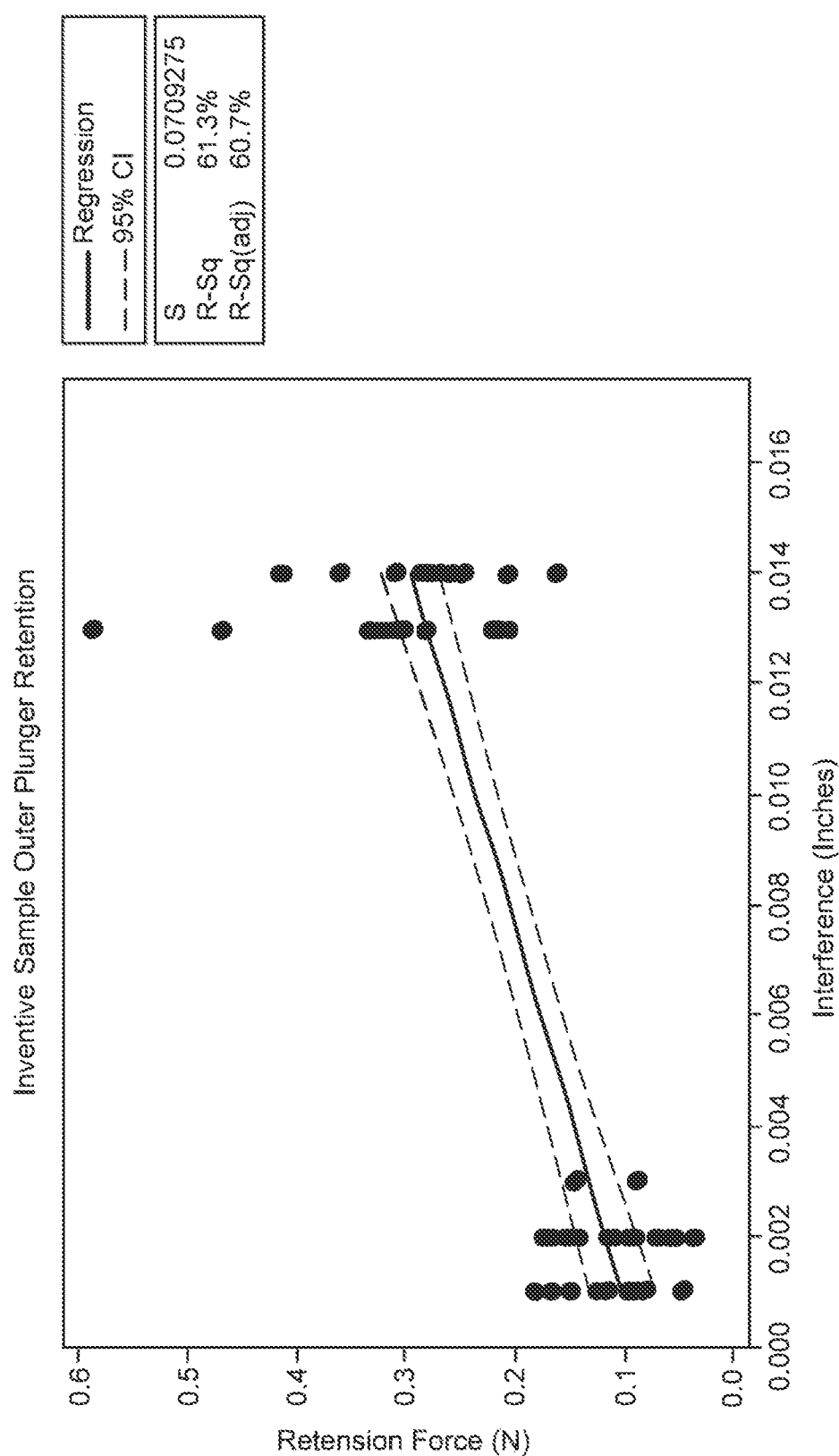
FIG. 35 is a chart showing Retention Force data for a tampon applicator of the present disclosure and prior art tampon applicators.
Figure 36:
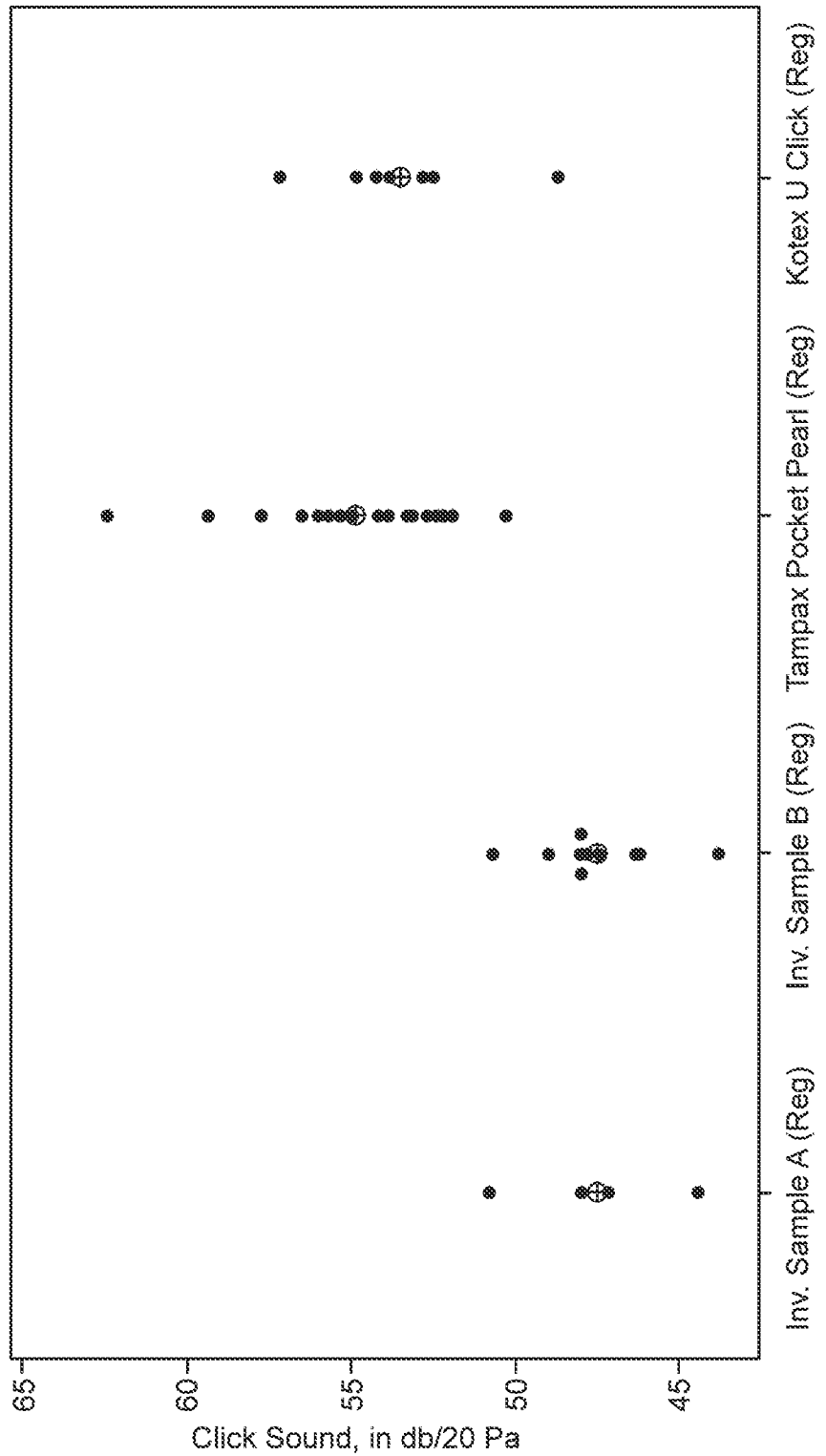
FIG. 36 is a chart showing "Click" sound comparison data for a tampon applicator of the present disclosure and prior art tampon applicators.

Referring to FIG. 35 and as described above, the Retention Force is another significant characteristic of compact applicators. The "Retention Force" is defined as the force required to overcome the at least partial connection between the inner sleeve 78 and the outer sleeve 76, in a non-deployed configuration, as the user draws the inner sleeve 78 rearward and/or outward from the outer sleeve 76. FIG. 35 describes retention as a correlation to the interference between the outer diameter (or connection mechanism 77 features on the outer diameter) of the inner sleeve 78 and inner diameter (or connection mechanism 77 features on the inner diameter) of the outer sleeve 76. As demonstrated by FIG. 35, the Inventive Sample A has a Retention Force in the range of about 0 N to 0.6 N, or more specifically, between about 0.01 N and about 0.4 N. Preferably, for production run applicators, the Retention Force is less than 3 N, and more preferably, the Retention Force is between about 0.01N and about 2.0 N. For clarity, the Retention Force is at least a factor of two less than the Click Force, and thus an indication that the Retention Force is adequately low.

The Retention Force can be determined using a scale such as an Instron Model 5944 or equivalent machine, and by following this procedure.

Procedure: Retention Force

1. Install the 100 N load cell on the Instron and calibrate.

2. Install the compact applicator assembly holder at the bottom jaw. The compact applicator assembly holder includes a fixture having at least two two lateral bores to receive at least two screws that retain the fixture to the Instron Model 5944. The fixture has a v-notched lead-in to a center grooved region sized to receive the grip region of the applicator barrel. The fixture plate has a thickness that corresponds to receive the length of the grip region. The grooved region is sized to receive the diameter of the grip region, including any protrusions the grip region may have.

3. Place grip region within the center grooved region such that it is secured within the grooved region.

4. Install hinged joint attachment fixture adjacent the compact applicator assembly holder such that the hinged joint attachment is located to receive the grip end of the inner sleeve. The hinged joint attachment fixture comprises a v-notched lead-in to a center groove sized and shaped to receive the grip end of the inner sleeve.

5. Insert the grip end of the inner sleeve into the hinged joint attachment fixture. Ensure the string is able to hang freely (i.e. it is not caught in the hinged joint attachment fixture and/or the compact applicator). When inserted and assembled, the compact applicator should be in a non-deployed position.

6. Zero out the force and extension.

7. Run the "Retention Force Assembly" Test. The upper jaw will move with a speed of 200 mm/min until the inner plunger locks into the outer plunger. Once the maximum load of 20N is reached, the upper jaw will stop moving.

The "Retention Force" will be shown by the first peak in the force data plotted by the computer associated with the Instron.

The Click Force is preferable as it provides one or more sensoral indicators that a deployed configuration has been achieved. Referring to FIG. 35, the Click Force has an auditory indicator. The "Click" sound achieved by the present disclosure is loud enough to confirm a deployed configuration has been achieved but is also quiet enough to enable discreet use of the product. Inventive Sample A having a flex latch 150 configuration, has an average sound of 47.5 db/20 Pa (where "20 Pa" is the sound pressure level). Inventive Sample B having a detent mechanism 128 as exemplified in FIGS. 10a-10b, also has an average sound of 47.5 db/20 Pa. Inventive Sample A and Inventive Sample B have a range of about 42 db/20 Pa to about 51 db/20 Pa. Kotex U Click had an average sound of 54.8 db/20 Pa, while Tampax Pocket had an average sound of about 53.5 db/20 Pa. Preferably, the click sound will be less than about 55 db/20 Pa. More preferably, the click sounds will be less than about 53.5 db/20 Pa. Preferably, the click sound will be greater than 0 db/20 Pa, and more preferably, the click sounds will be greater than about 42 db/20 Pa. More preferably between about 45 db/20 Pa and about 50 db/Pa.

A visual indicator is provided by seeing the flange 120 adjacent the detent mechanism 128, flange 124 between flange segments 120 and 122, and/or alignment of couplers 88a and 88b. A further visual indicator could include a color change due to the overlapping of the inner sleeve 78 and outer sleeve 76. In one embodiment, outer sleeve 76 has a first aesthetic, such that outer sleeve 76 is at least partially translucent, and/or has a first color or a first visual indicia. Timer sleeve is either partially translucent or opaque, and/or has a second color or second visual indicium that is different from the aesthetics on the outer sleeve 76. When the outer sleeve 76 and inner sleeve 78 are in a deployed configuration, the aesthetic of the overlapping region will be different than at least one of the first aesthetic and the second aesthetic. The deviation of aesthetics in the overlapping region will visually signal to the consumer that a deployed configuration has been achieved.

A tactile indicator is provided via the deflection of one of the inner sleeve 78 and outer sleeve 76 when they form a deployed configuration. Further tactile indicators can be provided such as a series of protrusions 130 or tabs 122 on either the outer surface of the inner sleeve 78 or on the inner surface of the outer sleeve 76. In one embodiment, the series would span a majority of the length of the inner sleeve 78 and/or outer sleeve 76 and spacing between protrusions 130 or tabs 122 would decrease along the length of the inner sleeve 78 and/or outer sleeve 76 in the direction of deployment. As the user withdraws the inner sleeve 78 rearward and/or outward from outer sleeve 76, the series would interact with one of couplers 88a and 88b, flanges 120 and 124, or other connection mechanism 77 such as a detent mechanism 128 as described throughout the present disclosure. The interaction would indicate to the consumer that she is gradually approaching the deployed configuration. In an alternate embodiment, the protrusions 130 or tabs 122 are concentrated near the couplers 88a and 88b, flanges 120 and 124, or other connection mechanisms 77 such as a detent mechanism 128 described throughout the present disclosure. The interaction would indicate to the consumer that she is on the precipice of the deployed configuration.

Another concern with compact applicators is the strength of the inner sleeve 78 and outer sleeve 76 in a deployed configuration. It is important that the assembled plunger does not collapse on itself prior to ejecting the tampon (i.e. the inner sleeve 78 does telescope into the outer sleeve 76). The "Collapse Force" describes the force required to disengage the inner sleeve 78 and outer sleeve 76 from a deployed position. Inventive Sample A, Kotex U Click and Tampax Pocket samples, Regular Absorbency, were tested to determine Collapse Force as it relates to Ejection Force. Inventive Sample A was found to have an average Collapse Force of 31.3 N, with a standard deviation of 6.68 N, and an average Ejection Force of about 4.15 N, with a standard deviation of about 0.16 N. As such, Inventive Sample A has a safety factor of about 7.5, indicating a reliable design (i.e. the plunger will not collapse as it has would require a force about 7.5 times greater than the force required to eject the tampon). Kotex U Click samples achieved the highest Collapse Force of 61.8 N, with a standard deviation of about 10.8 N, and an average Ejection Force of about 2.48N, with a standard deviation of about 0.36 N. Tampax Pocket samples achieved a Collapse Force of about 42.7 N, with a standard deviation of about 15.3 N, and an average Ejection Force of about 2.93 N, with a standard deviation of about 0.71 N. As such, the Collapse Force should have a safety factor of at least 5 and more preferably at least about 7.

The "Ejection Force" is described as the force required to eject a tampon from the applicator. The Ejection Force can be determined using a scale such as a Tronix scale model #WI-130, and by following this procedure:

Procedure: Ejection Force
1. Zero out the scale and ensure it is weighing in ounces (other units of Force are also acceptable, such as Newtons).
2. Grasp the applicator (containing a tampon) by the finger grip using the thumb and index finger. Place the applicator, plunger end down, on top of the balance platform. Apply a steady downward motion until the tampon is ejected from the barrel. Apply the least amount of pressure possible, while ejecting the tampon from the barrel.
3. Record the maximum Ejection Force indicated by the scale (Note: the Ejection Force is recorded automatically if the scale is used in conjunction with computer running data collection software).

The present disclosure is advantageous in that is harmonizes a plurality of competing factors: low Click Force, high Collapse Force, and low volume Click sound, and maximizes full-size applicator features.

One skilled in the art understands the compact applicator assembly of the present disclosure can comprise a plurality of materials and aesthetics. In particular, using aesthetics to elicit distinction amongst components of the applicator system can be advantageous. For instance, in one embodiment the grip region has a distinct aesthetic and/or tactile indicators (i.e. a material, texture, color, tone, shade, luminosity, print, pattern, graphic or other visual indicators) on with respect to the rest of the applicator barrel can assist the user in identifying where and how to hold the tampon applicator. In another embodiment, one or more parts of the applicator assembly are at least partially translucent to assist the user in identifying where aspects of the applicator are (i.e. where the tampon and/or tampon string are located within the applicator, and/or where the inner sleeve is positioned in a compact configuration versus a deployed configuration). In further embodiments, the inner sleeve and outer sleeve may have different visual and/or tactile indicators.

Although this invention has been shown and described with respect to the detailed embodiments thereof, it will be understood by those skilled in the art that various changes in form and detail may be made without departing from the spirit and scope of the invention.

The invention claimed is:

1. A tampon applicator, comprising:
 a barrel defining an interior cavity, the barrel extending lengthwise between a plunger end and an insertion end, the barrel including a grip region, a transition region, a main body region, a plurality of petals, wherein the transition region is disposed between the main body region and the grip region, and the petals are disposed between the insertion end and the main body region; and
 a telescoping two-piece plunger that includes an outer sleeve and an inner sleeve having a digit portion, wherein the plunger is configured to selectively reside in a non-deployed configuration or a deployed configuration, wherein in the non-deployed configuration substantially all of the inner sleeve is disposed within the outer sleeve and substantially all of the outer sleeve is disposed within the interior cavity of the barrel, and in the deployed configuration, substantially all of the inner sleeve is disposed outside the outer sleeve.

2. The tampon applicator of claim 1, wherein the deployed configuration is achieved with a Click Force of between about 3 N and about 7 N.

3. The tampon applicator of claim 1, wherein the two-piece plunger has a Retention Force of between about 0.01 N and about 2N.

4. The tampon applicator of claim 1, wherein the deployed configuration is achieved with a Click sound of between about 42 db/20 PA and about 53 db/20 PA.

5. The tampon applicator of claim 1, wherein said two-piece plunger has a connection mechanism permitting the deployed configuration.

6. A tampon applicator, comprising:
 a barrel extending lengthwise between a plunger end and an insertion end, the barrel including a grip region, a transition region, a main body region, a plurality of petals, and
 an interior cavity, wherein the transition region is disposed between the main body region and the grip region, and the petals are disposed between the insertion end and the main body region; and
 a telescoping two-piece plunger that includes an outer sleeve and an inner sleeve, wherein the sleeves are selectively actuable into a deployed configuration in which the inner and outer sleeves are combined into a unitary member, and wherein the inner sleeve has a stem portion with a length and a digit portion;
 wherein in the deployed configuration the plunger is selectively movable in a lengthwise direction relative to the barrel a full stroke travel to fully elect an absorbent tampon housed inside the barrel, which full stroke travel is substantially equal to the length of the inner sleeve stem portion.

7. The tampon applicator of claim 6, wherein the deployed configuration is achieved with a Click Force of between about 3 N and about 7 N.

8. The tampon applicator of claim 6, wherein the two-piece plunger has a Retention Force of between about 0.01 N and about 2N.

9. The tampon applicator of claim 6, wherein the deployed configuration is achieved with a Click sound of between about 42 db/20 PA and about 53 db/20 PA.

10. The tampon applicator of claim 6, wherein said two-piece plunger has a connection mechanism permitting the deployed configuration.

11. A compact tampon applicator assembly, comprising:
an absorbent tampon having a length;
an applicator, comprising:
a barrel defining a cavity having the tampon therein, the barrel extending lengthwise between a plunger end and an insertion end, the barrel including a grip region adjacent a main body region, and a plurality of petals disposed between the insertion end and the main body region; and
a telescoping two-piece plunger comprising an outer sleeve and an inner sleeve, wherein the plunger is configured to selectively reside in a non-deployed configuration or a deployed configuration,
wherein the inner sleeve has a leading end and a digit portion that is opposite the leading end, wherein the inner sleeve has an inner coupler located proximal the leading end;
wherein the outer sleeve has a pledget end located within the applicator barrel and the outer sleeve has a trailing end opposite to the pledget end, the outer sleeve having an outer coupler located proximal the trailing end;
wherein the inner coupler and the outer coupler engage when the inner sleeve is drawn rearwardly by the digit portion in forming the deployed configuration; and
wherein substantially all of the outer sleeve is disposed inside the barrel in the deployed configuration.

12. The tampon applicator of claim 11, wherein substantially all of the outer sleeve is disposed inside the barrel in the non-deployed configuration.

13. The tampon applicator of claim 11, wherein the two-piece plunger has a Retention Force of between about 0.01 N and about 2N.

14. The tampon applicator of claim 11, wherein the deployed configuration is achieved with a Click sound of between about 42 db/20 PA and about 53 db/20 PA.

15. The tampon applicator of claim 11, wherein the deployed configuration where the inner coupler and the outer coupler are engaged is achieved with a Click Force of between about 3 N and about 7 N.

\* \* \* \* \*